United States Patent
Jara et al.

(10) Patent No.: US 9,910,049 B2
(45) Date of Patent: *Mar. 6, 2018

(54) DETECTION OF MISFOLDED AMYLOID BETA PROTEIN

(71) Applicants: Board of Regents of the University of Texas System, Austin, TX (US); Amprion, Inc., Houston, TX (US)

(72) Inventors: Claudio Soto Jara, Friendswood, TX (US); Mohammad Shahnawaz, Houston, TX (US); Russell M. Lebovitz, Oakland, CA (US); Benedikt K. Vollrath, San Diego, CA (US)

(73) Assignees: AMPRION, INC., San Diego, CA (US); THE BOARD OF REGENTS OF THE UNIVERSITY OF TEXAS SYSTEM, Austin, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/852,471

(22) Filed: Sep. 11, 2015

(65) Prior Publication Data

US 2016/0077110 A1     Mar. 17, 2016

Related U.S. Application Data

(60) Provisional application No. 62/049,303, filed on Sep. 11, 2014.

(51) Int. Cl.
    *G01N 33/68*     (2006.01)

(52) U.S. Cl.
    CPC . *G01N 33/6896* (2013.01); *G01N 2333/4709* (2013.01); *G01N 2800/2821* (2013.01); *G01N 2800/52* (2013.01)

(58) Field of Classification Search
    CPC ....... G01N 33/6896; G01N 2800/2821; G01N 2333/4709; G01N 2800/52; G01N 2500/00
    See application file for complete search history.

(56) References Cited

U.S. PATENT DOCUMENTS

| 7,351,526 B2 | 4/2008 | Soto et al. | |
| 2008/0118938 A1* | 5/2008 | Estrada | G01N 33/6896 435/7.92 |
| 2011/0166035 A1* | 7/2011 | Kleinschmidt | C07K 14/4711 506/9 |

OTHER PUBLICATIONS

Ghiso J et al. Alzheimer's soluble amyloid beta is a normal component of human urine. FEBS Lett. 1997, 408:105-108.*

Moreno-Gonzales I et al. Misfolded protein aggregates: Mechanisms, structures and potential for disease transmission. Seminars Cell Dev. Biol. 2011, 22:482-487.*

Salvadores N et al. Detection of misfolded Abeta oligomers for sensitive biochemical diagnosis of Alzheimer's disease. Cell Reports, Apr. 2014, 7:261-268.*

Winblad B et al. Active immunotherapy options for Alzheimer's disease. Alzheimer's Res. Therap. Jan. 2014, 6:7 (12 pages).*

Zhou P et al. Immunoassays with protein misfolding cycle amplification: A platform for ultrasensitive detection of antigen. Analytical Chem. 2012, 84:7343-7349.*

Garvey M et al. Phosphate and HEPES buffers potently affect the fibrillation and oligomerization mechanism of Alzheimer's Abeta peptide. Biochem Biophys Res Comm, 2011, 409:385-388.*

Jimenez S et al. Disruption of amyloid plaques integrity affects the soluble oligomers content from Alzheimer disease brains. PLoS ONE, 2014, 9(12):e114041.*

Padayachee ER et al. The novel effect of CSF and APOE4 on the aggregation kinetics of Abeta42 in Alzheimer's disease. Alzheimer's & Dementia, Jul. 2014, 10 (Suppl. 4):P511, Poster Abstract P2-108, Alzheimer's Association International Conference 2014.*

Paravastu AK et al. Seeded growth of beta-amyloid fibrils from Alzheimer's brain-derived fibrils produces a distinct fibril structure. Proc. Natl. Acad. Sci. USA, 2009, 106(18):7443-7448.*

Schmidt M et al. Comparison of Alzheimer Abeta(1-40) and Abeta(1-42) amyloid fibrils reveals similar protofilament structures. Proc Natl Acad Sci USA, 2009, 106(47):19813-19818.*

Castilla, et. al. "Protein Misfolding Cyclic Amplification for Diagnosis and Prion Propagation Studies" Methods Enzymol., 2006, 412, 3-21.

Office action issued in SOTO, U.S. Pat. No. 7,351,526; dated Apr. 13, 2007.

* cited by examiner

*Primary Examiner* — Kimberly A. Ballard
(74) *Attorney, Agent, or Firm* — Benjamen E. Kern; Kraig K. Anderson

(57) ABSTRACT

Methods and kits are provided for amplifying and detecting Aβ proteins from samples, for example, from patients having Alzheimer's Disease. For example, a method for determining a presence of a soluble, misfolded Aβ protein may include contacting the sample with a monomeric, folded Aβ protein to form an incubation mixture; conducting an incubation cycle two or more times on the incubation mixture effective to form an amplified portion of misfolded Aβ protein; incubating the incubation mixture effective to cause misfolding and/or aggregation of at least a portion of the monomeric, folded Aβ protein; physically disrupting the incubation mixture effective to at least partly de-aggregate at least a portion of a misfolded Aβ aggregate present; and determining the presence of the soluble, misfolded Aβ protein in the sample by detecting at least a portion of the amplified portion of misfolded Aβ protein.

22 Claims, 18 Drawing Sheets

Table 1: Estimation of sensitivity, specificity, and predictive value for Aβ-PCMA in CSF[1]

| GROUPS | SENSITIVITY[2] | SPECIFICITY[2] | POSITIVE PREDICTIVE VALUE[2] | NEGATIVE PREDICTIVE VALUE[2] |
|---|---|---|---|---|
| AD vs NAND | 100.0% | 94.6% | 96.2% | 100.0% |
| AD vs NND | 90.0% | 84.2% | 88.2% | 86.5% |
| AD vs controls[3] | 90.0% | 92.0% | 88.2% | 93.2% |

1. For estimation of sensitivity, specificity and predictive value the results of the lag phase as shown in FIG. 9B were used. Cutoffs were estimated by Receiver Operating Characteristics (ROC) curve analysis using the MedCalc software.

2. Sensitivity was estimated by the formula: [True positives/(True positives + False negatives)] x 100; specificity was estimated by the formula: [True negatives/(False positives + True negatives)] x 100; positive predictive value was estimated by the formula: [True positives/(True positives + False positives)] x 100; negative predictive value was estimated by the formula: [True negatives/(True negatives + False negatives)] x 100

3. Controls refers to the samples from NND plus NAND.

FIG. 5

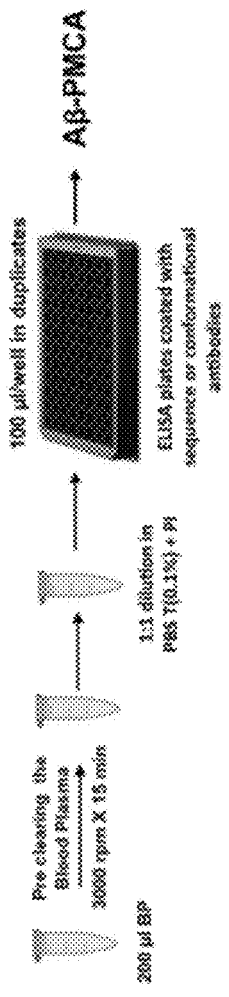
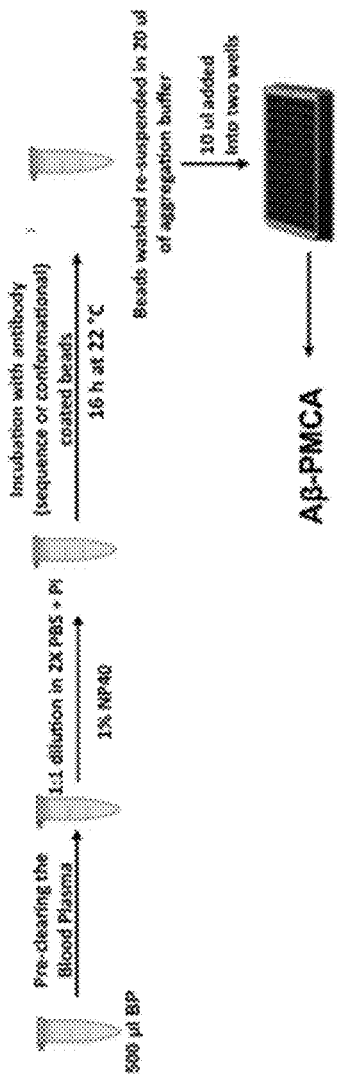
FIG. 8A
FIG. 8B

Table 2

DAEFRHDSGYEVHHQKLVFFAEDVGSNKGAIIGLMVGGVVIA

| Antibody | Epitope | Commercial source | Aβ oligomer capturing capacity |
|---|---|---|---|
| 82E1 | 1-5 | IBL America | +++ |
| 4G8 | 18-22 | Covance | + |
| 6E10 | 3-8 | Covance | ++ |
| X-40/42 | C-terminal | Mybiosource | - |
| 16 ADV Mouse IgG1 | Conformational | Acumen | ++ |
| A11 | Conformational | Invitrogen | - |

+++ Best
++ very good
+ good
- no result

FIG. 9

```
                        SEQUENCE LISTING

<160> NUMBER OF SEQ ID NOS: 20

<210> SEQ ID NO 1
<211> LENGTH: 770
<212> TYPE: PRT
<213> ORGANISM: Homo sapiens
<300> PUBLICATION INFORMATION:
<308> DATABASE ACCESSION NUMBER: Uniprot
<309> DATABASE ENTRY DATE: 1991-11-01
<313> RELEVANT RESIDUES IN SEQ ID NO: (1)..(770)

<400> SEQUENCE: 1

Met Leu Pro Gly Leu Ala Leu Leu Leu Ala Ala Trp Thr Ala Arg
1               5                   10                  15

Ala Leu Glu Val Pro Thr Asp Gly Asn Ala Gly Leu Leu Ala Glu Pro
            20                  25                  30

Gln Ile Ala Met Phe Cys Gly Arg Leu Asn Met His Met Asn Val Gln
        35                  40                  45

Asn Gly Lys Trp Asp Ser Asp Pro Ser Gly Thr Lys Thr Cys Ile Asp
    50                  55                  60

Thr Lys Glu Gly Ile Leu Gln Tyr Cys Gln Glu Val Tyr Pro Glu Leu
65                  70                  75                  80

Gln Ile Thr Asn Val Val Glu Ala Asn Gln Pro Val Thr Ile Gln Asn
                85                  90                  95

Trp Cys Lys Arg Gly Arg Lys Gln Cys Lys Thr His Pro His Phe Val
            100                 105                 110

Ile Pro Tyr Arg Cys Leu Val Gly Glu Phe Val Ser Asp Ala Leu Leu
        115                 120                 125

Val Pro Asp Lys Cys Lys Phe Leu His Gln Glu Arg Met Asp Val Cys
    130                 135                 140

Glu Thr His Leu His Trp His Thr Val Ala Lys Glu Thr Cys Ser Glu
145                 150                 155                 160

Lys Ser Thr Asn Leu His Asp Tyr Gly Met Leu Leu Pro Cys Gly Ile
                165                 170                 175

Asp Lys Phe Arg Gly Val Glu Phe Val Cys Gln Pro Leu Ala Glu Glu
            180                 185                 190
```

-continued

```
Ser Asp Asn Val Asp Ser Ala Asp Ala Glu Glu Asp Ser Asp Val
        195                 200                 205
Trp Trp Gly Gly Ala Asp Thr Asp Tyr Ala Asp Gly Ser Glu Asp Lys
    210                 215                 220
Val Val Glu Val Ala Glu Glu Glu Val Ala Glu Val Glu Glu Glu
225                 230                 235                 240
Glu Ala Asp Asp Asp Glu Asp Asp Glu Asp Gly Asp Glu Val Glu Glu
                245                 250                 255
Glu Ala Glu Glu Pro Tyr Glu Ala Thr Glu Arg Thr Thr Ser Ile
            260                 265                 270
Ala Thr Thr Thr Thr Thr Thr Glu Ser Val Glu Val Val Arg
        275                 280                 285
Glu Val Cys Ser Glu Gln Ala Glu Thr Gly Pro Cys Arg Ala Met Ile
        290                 295                 300
Ser Arg Trp Tyr Phe Asp Val Thr Glu Gly Lys Cys Ala Pro Phe Phe
305                 310                 315                 320
Tyr Gly Gly Cys Gly Asn Arg Asn Asn Phe Asp Thr Glu Glu Tyr
            325                 330                 335
Cys Met Ala Val Cys Gly Ser Ala Met Ser Gln Ser Leu Leu Lys Thr
            340                 345                 350
Thr Gln Glu Pro Leu Ala Arg Asp Pro Val Lys Leu Pro Thr Thr Ala
        355                 360                 365
Ala Ser Thr Pro Asp Ala Val Asp Lys Tyr Leu Glu Thr Pro Gly Asp
    370                 375                 380
Glu Asn Glu His Ala His Phe Gln Lys Ala Lys Glu Arg Leu Glu Ala
385                 390                 395                 400
Lys His Arg Glu Arg Met Ser Gln Val Met Arg Glu Trp Glu Glu Ala
                405                 410                 415
Glu Arg Gln Ala Lys Asn Leu Pro Lys Ala Asp Lys Lys Ala Val Ile
            420                 425                 430
Gln His Phe Gln Glu Lys Val Glu Ser Leu Glu Gln Glu Ala Ala Asn
        435                 440                 445
Glu Arg Gln Gln Leu Val Glu Thr His Met Ala Arg Val Glu Ala Met
        450                 455                 460
Leu Asn Asp Arg Arg Arg Leu Ala Leu Glu Asn Tyr Ile Thr Ala Leu
465                 470                 475                 480
Gln Ala Val Pro Pro Arg Pro Arg His Val Phe Asn Met Leu Lys Lys
            485                 490                 495
Tyr Val Arg Ala Glu Gln Lys Asp Arg Gln His Thr Leu Lys His Phe
            500                 505                 510
Glu His Val Arg Met Val Asp Pro Lys Lys Ala Ala Gln Ile Arg Ser
        515                 520                 525
Gln Val Met Thr His Leu Arg Val Ile Tyr Glu Arg Met Asn Gln Ser
    530                 535                 540
Leu Ser Leu Leu Tyr Asn Val Pro Ala Val Ala Glu Glu Ile Gln Asp
545                 550                 555                 560
Glu Val Asp Glu Leu Leu Gln Lys Glu Gln Asn Tyr Ser Asp Asp Val
                565                 570                 575
Leu Ala Asn Met Ile Ser Glu Pro Arg Ile Ser Tyr Gly Asn Asp Ala
            580                 585                 590
Leu Met Pro Ser Leu Thr Glu Thr Lys Thr Thr Val Glu Leu Leu Pro
        595                 600                 605
```

```
Val Asn Gly Glu Phe Ser Leu Asp Asp Leu Gln Pro Trp His Ser Phe
    610                 615                 620

Gly Ala Asp Ser Val Pro Ala Asn Thr Glu Asn Glu Val Glu Pro Val
625                 630                 635                 640

Asp Ala Arg Pro Ala Ala Asp Arg Gly Leu Thr Thr Arg Pro Gly Ser
                645                 650                 655

Gly Leu Thr Asn Ile Lys Thr Glu Glu Ile Ser Glu Val Lys Met Asp
                660                 665                 670

Ala Glu Phe Arg His Asp Ser Gly Tyr Glu Val His His Gln Lys Leu
                675                 680                 685

Val Phe Phe Ala Glu Asp Val Gly Ser Asn Lys Gly Ala Ile Ile Gly
    690                 695                 700

Leu Met Val Gly Gly Val Val Ile Ala Thr Val Ile Val Ile Thr Leu
705                 710                 715                 720

Val Met Leu Lys Lys Lys Gln Tyr Thr Ser Ile His His Gly Val Val
                725                 730                 735

Glu Val Asp Ala Ala Val Thr Pro Glu Glu Arg His Leu Ser Lys Met
                740                 745                 750

Gln Gln Asn Gly Tyr Glu Asn Pro Thr Tyr Lys Phe Phe Glu Gln Met
                755                 760                 765

Gln Asn
    770

<210> SEQ ID NO 2
<211> LENGTH: 40
<212> TYPE: PRT
<213> ORGANISM: Homo sapiens
<300> PUBLICATION INFORMATION:
<301> AUTHORS: Mahiuddin Ahmed, Judianne Davis, Darryl Aucoin, Takeshi
      Sato, Shivani Ahuja, Saburo Aimoto, James I Elliott, William E Van
      Nostrand, Steven O Smith,
<302> TITLE: Structural Conversion of Neurotoxic Amyloid-Beta 1-42
      Oligomers to Fibrils
<303> JOURNAL: Nature Structural & Molecular Biology
<304> VOLUME: 17
<306> PAGES: 561-567
<307> DATE: 2010
<300> PUBLICATION INFORMATION:
<301> AUTHORS: Mahiuddin Ahmed, Judianne Davis, Darryl Aucoin, Takeshi
      Sato, Shivani Ahuja, Saburo Aimoto, James I Elliott, William E Van
      Nostrand, Steven O Smith,
<302> TITLE: Human Amyloid-Beta Synthesis and Clearance Rates as
      Measured in Cerebrospinal Fluid in vivo
<303> JOURNAL: Nature Medicine
<304> VOLUME: 12
<306> PAGES: 856-861
<307> DATE: 2006

<400> SEQUENCE: 2

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val
        35                  40

<210> SEQ ID NO 3
<211> LENGTH: 42
<212> TYPE: PRT
<213> ORGANISM: Homo sapiens
<300> PUBLICATION INFORMATION:
<301> AUTHORS: Mahiuddin Ahmed, Judianne Davis, Darryl Aucoin, Takeshi
      Sato, Shivani Ahuja, Saburo Aimoto, James I Elliott, William E Van
      Nostrand, Steven O Smith
```

```
<302> TITLE: Structural Conversion of Neurotoxic Amyloid-Beta 1-42
      Oligomers to Fibrils
<303> JOURNAL: Nature Structural & Molecular Biology
<304> VOLUME: 17
<306> PAGES: 561-567
<307> DATE: 2010
<300> PUBLICATION INFORMATION:
<301> AUTHORS: Randall J Bateman, Ling Y Munsell, John C Morris, Robert
      Swarm, Kevin E Yarasheski, David M Holtzman
<302> TITLE: Human Amyloid-Beta Synthesis and Clearance Rates as
      Measured in Cerebrospinal Fluid in vivo
<303> JOURNAL: Nature Medicine
<304> VOLUME: 12
<306> PAGES: 856-861
<307> DATE: 2006

<400> SEQUENCE: 3

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val Ile Ala
            35                  40

<210> SEQ ID NO 4
<211> LENGTH: 758
<212> TYPE: PRT
<213> ORGANISM: Homo sapiens
<300> PUBLICATION INFORMATION:
<308> DATABASE ACCESSION NUMBER: Uniprot
<309> DATABASE ENTRY DATE: 2011-05-31
<313> RELEVANT RESIDUES IN SEQ ID NO: (1)..(758)

<400> SEQUENCE: 4

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Glu Ser Pro Leu
        35                  40                  45

Gln Thr Pro Thr Glu Asp Gly Ser Glu Glu Pro Gly Ser Glu Thr Ser
    50                  55                  60

Asp Ala Lys Ser Thr Pro Thr Ala Glu Asp Val Thr Ala Pro Leu Val
65                  70                  75                  80

Asp Glu Gly Ala Pro Gly Lys Gln Ala Ala Ala Gln Pro His Thr Glu
                85                  90                  95

Ile Pro Glu Gly Thr Thr Ala Glu Glu Ala Gly Ile Gly Asp Thr Pro
            100                 105                 110

Ser Leu Glu Asp Glu Ala Ala Gly His Val Thr Gln Glu Pro Glu Ser
        115                 120                 125

Gly Lys Val Val Gln Glu Gly Phe Leu Arg Glu Pro Gly Pro Pro Gly
    130                 135                 140

Leu Ser His Gln Leu Met Ser Gly Met Pro Gly Ala Pro Leu Leu Pro
145                 150                 155                 160

Glu Gly Pro Arg Glu Ala Thr Arg Gln Pro Ser Gly Thr Gly Pro Glu
                165                 170                 175

Asp Thr Glu Gly Gly Arg His Ala Pro Glu Leu Leu Lys His Gln Leu
            180                 185                 190

Leu Gly Asp Leu His Gln Glu Gly Pro Pro Leu Lys Gly Ala Gly Gly
        195                 200                 205

Lys Glu Arg Pro Gly Ser Lys Glu Glu Val Asp Glu Asp Arg Asp Val
```

```
            210                 215                 220
Asp Glu Ser Ser Pro Gln Asp Ser Pro Pro Ser Lys Ala Ser Pro Ala
225                 230                 235                 240

Gln Asp Gly Arg Pro Gln Thr Ala Ala Arg Glu Ala Thr Ser Ile
            245                 250                 255

Pro Gly Phe Pro Ala Glu Gly Ala Ile Pro Leu Pro Val Asp Phe Leu
            260                 265                 270

Ser Lys Val Ser Thr Glu Ile Pro Ala Ser Glu Pro Asp Gly Pro Ser
            275                 280                 285

Val Gly Arg Ala Lys Gly Gln Asp Ala Pro Leu Glu Phe Thr Phe His
            290                 295                 300

Val Glu Ile Thr Pro Asn Val Gln Lys Glu Gln Ala His Ser Glu Glu
305                 310                 315                 320

His Leu Gly Arg Ala Ala Phe Pro Gly Ala Pro Gly Glu Gly Pro Glu
            325                 330                 335

Ala Arg Gly Pro Ser Leu Gly Glu Asp Thr Lys Glu Ala Asp Leu Pro
            340                 345                 350

Glu Pro Ser Glu Lys Gln Pro Ala Ala Ala Pro Arg Gly Lys Pro Val
            355                 360                 365

Ser Arg Val Pro Gln Leu Lys Ala Arg Met Val Ser Lys Ser Lys Asp
            370                 375                 380

Gly Thr Gly Ser Asp Asp Lys Lys Ala Lys Thr Ser Thr Arg Ser Ser
385                 390                 395                 400

Ala Lys Thr Leu Lys Asn Arg Pro Cys Leu Ser Pro Lys His Pro Thr
            405                 410                 415

Pro Gly Ser Ser Asp Pro Leu Ile Gln Pro Ser Ser Pro Ala Val Cys
            420                 425                 430

Pro Glu Pro Pro Ser Ser Pro Lys Tyr Val Ser Ser Val Thr Ser Arg
            435                 440                 445

Thr Gly Ser Ser Gly Ala Lys Glu Met Lys Leu Lys Gly Ala Asp Gly
            450                 455                 460

Lys Thr Lys Ile Ala Thr Pro Arg Gly Ala Ala Pro Pro Gly Gln Lys
465                 470                 475                 480

Gly Gln Ala Asn Ala Thr Arg Ile Pro Ala Lys Thr Pro Pro Ala Pro
            485                 490                 495

Lys Thr Pro Pro Ser Ser Gly Glu Pro Pro Lys Ser Gly Asp Arg Ser
            500                 505                 510

Gly Tyr Ser Ser Pro Gly Ser Pro Gly Thr Pro Gly Ser Arg Ser Arg
            515                 520                 525

Thr Pro Ser Leu Pro Thr Pro Pro Thr Arg Glu Pro Lys Lys Val Ala
            530                 535                 540

Val Val Arg Thr Pro Pro Lys Ser Pro Ser Ser Ala Lys Ser Arg Leu
545                 550                 555                 560

Gln Thr Ala Pro Val Pro Met Pro Asp Leu Lys Asn Val Lys Ser Lys
            565                 570                 575

Ile Gly Ser Thr Glu Asn Leu Lys His Gln Pro Gly Gly Gly Lys Val
            580                 585                 590

Gln Ile Ile Asn Lys Lys Leu Asp Leu Ser Asn Val Gln Ser Lys Cys
            595                 600                 605

Gly Ser Lys Asp Asn Ile Lys His Val Pro Gly Gly Gly Ser Val Gln
            610                 615                 620

Ile Val Tyr Lys Pro Val Asp Leu Ser Lys Val Thr Ser Lys Cys Gly
625                 630                 635                 640
```

-continued

```
Ser Leu Gly Asn Ile His His Lys Pro Gly Gly Gln Val Glu Val
                645                 650                 655

Lys Ser Glu Lys Leu Asp Phe Lys Asp Arg Val Gln Ser Lys Ile Gly
            660                 665                 670

Ser Leu Asp Asn Ile Thr His Val Pro Gly Gly Gly Asn Lys Lys Ile
            675                 680                 685

Glu Thr His Lys Leu Thr Phe Arg Glu Asn Ala Lys Ala Lys Thr Asp
            690                 695                 700

His Gly Ala Glu Ile Val Tyr Lys Ser Pro Val Val Ser Gly Asp Thr
705                 710                 715                 720

Ser Pro Arg His Leu Ser Asn Val Ser Ser Thr Gly Ser Ile Asp Met
                725                 730                 735

Val Asp Ser Pro Gln Leu Ala Thr Leu Ala Asp Glu Val Ser Ala Ser
                740                 745                 750

Leu Ala Lys Gln Gly Leu
            755

<210> SEQ ID NO 5
<211> LENGTH: 316
<212> TYPE: PRT
<213> ORGANISM: Homo sapiens
<300> PUBLICATION INFORMATION:
<308> DATABASE ACCESSION NUMBER: Uniprot
<309> DATABASE ENTRY DATE: 2011-05-31
<313> RELEVANT RESIDUES IN SEQ ID NO: (1)..(316)

<400> SEQUENCE: 5

Met Leu Arg Ala Leu Gln Gln Arg Lys Arg Glu Ala Gly Ile Gly Asp
1               5                   10                  15

Thr Pro Ser Leu Glu Asp Glu Ala Ala Gly His Val Thr Gln Ala Arg
            20                  25                  30

Met Val Ser Lys Ser Lys Asp Gly Thr Gly Ser Asp Asp Lys Lys Ala
        35                  40                  45

Lys Gly Ala Asp Gly Lys Thr Lys Ile Ala Thr Pro Arg Gly Ala Ala
    50                  55                  60

Pro Pro Gly Gln Lys Gly Gln Ala Asn Ala Thr Arg Ile Pro Ala Lys
65                  70                  75                  80

Thr Pro Pro Ala Pro Lys Thr Pro Pro Ser Ser Gly Glu Pro Pro Lys
                85                  90                  95

Ser Gly Asp Arg Ser Gly Tyr Ser Ser Pro Gly Ser Pro Gly Thr Pro
            100                 105                 110

Gly Ser Arg Ser Arg Thr Pro Ser Leu Pro Thr Pro Pro Thr Arg Glu
        115                 120                 125

Pro Lys Lys Val Ala Val Val Arg Thr Pro Pro Lys Ser Pro Ser Ser
    130                 135                 140

Ala Lys Ser Arg Leu Gln Thr Ala Pro Val Pro Met Pro Asp Leu Lys
145                 150                 155                 160

Asn Val Lys Ser Lys Ile Gly Ser Thr Glu Asn Leu Lys His Gln Pro
                165                 170                 175

Gly Gly Gly Lys Val Gln Ile Val Tyr Lys Pro Val Asp Leu Ser Lys
            180                 185                 190

Val Thr Ser Lys Cys Gly Ser Leu Gly Asn Ile His His Lys Pro Gly
        195                 200                 205

Gly Gly Gln Val Glu Val Lys Ser Glu Lys Leu Asp Phe Lys Asp Arg
    210                 215                 220
```

```
Val Gln Ser Lys Ile Gly Ser Leu Asp Asn Ile Thr His Val Pro Gly
225                 230                 235                 240

Gly Gly Asn Lys Lys Ile Glu Thr His Lys Leu Thr Phe Arg Glu Asn
            245                 250                 255

Ala Lys Ala Lys Thr Asp His Gly Ala Glu Ile Val Tyr Lys Ser Pro
        260                 265                 270

Val Val Ser Gly Asp Thr Ser Pro Arg His Leu Ser Asn Val Ser Ser
    275                 280                 285

Thr Gly Ser Ile Asp Met Val Asp Ser Pro Gln Leu Ala Thr Leu Ala
290                 295                 300

Asp Glu Val Ser Ala Ser Leu Ala Lys Gln Gly Leu
305                 310                 315

<210> SEQ ID NO 6
<211> LENGTH: 381
<212> TYPE: PRT
<213> ORGANISM: Homo sapiens
<300> PUBLICATION INFORMATION:
<308> DATABASE ACCESSION NUMBER: Uniprot
<309> DATABASE ENTRY DATE: 2011-05-31
<313> RELEVANT RESIDUES IN SEQ ID NO: (1)..(381)

<400> SEQUENCE: 6

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Glu Ser Pro Leu
        35                  40                  45

Gln Thr Pro Thr Glu Asp Gly Ser Glu Glu Pro Gly Ser Glu Thr Ser
    50                  55                  60

Asp Ala Lys Ser Thr Pro Thr Ala Glu Ala Glu Ala Gly Ile Gly
65                  70                  75                  80

Asp Thr Pro Ser Leu Glu Asp Glu Ala Ala Gly His Val Thr Gln Ala
                85                  90                  95

Arg Met Val Ser Lys Ser Lys Asp Gly Thr Gly Ser Asp Asp Lys Lys
            100                 105                 110

Ala Lys Gly Ala Asp Gly Lys Thr Lys Ile Ala Thr Pro Arg Gly Ala
        115                 120                 125

Ala Pro Pro Gly Gln Lys Gly Gln Ala Asn Ala Thr Arg Ile Pro Ala
    130                 135                 140

Lys Thr Pro Pro Ala Pro Lys Thr Pro Pro Ser Ser Gly Glu Pro Pro
145                 150                 155                 160

Lys Ser Gly Asp Arg Ser Gly Tyr Ser Ser Pro Gly Ser Pro Gly Thr
                165                 170                 175

Pro Gly Ser Arg Ser Arg Thr Pro Ser Leu Pro Thr Pro Pro Thr Arg
            180                 185                 190

Glu Pro Lys Lys Val Ala Val Val Arg Thr Pro Pro Lys Ser Pro Ser
        195                 200                 205

Ser Ala Lys Ser Arg Leu Gln Thr Ala Pro Val Pro Met Pro Asp Leu
    210                 215                 220

Lys Asn Val Lys Ser Lys Ile Gly Ser Thr Glu Asn Leu Lys His Gln
225                 230                 235                 240

Pro Gly Gly Gly Lys Val Gln Ile Val Tyr Lys Pro Val Asp Leu Ser
                245                 250                 255

Lys Val Thr Ser Lys Cys Gly Ser Leu Gly Asn Ile His His Lys Pro
```

```
                260                 265                 270
Gly Gly Gly Gln Val Glu Val Lys Ser Glu Lys Leu Asp Phe Lys Asp
            275                 280                 285

Arg Val Gln Ser Lys Ile Gly Ser Leu Asp Asn Ile Thr His Val Pro
        290                 295                 300

Gly Gly Gly Asn Lys Lys Ile Glu Thr His Lys Leu Thr Phe Arg Glu
305                 310                 315                 320

Asn Ala Lys Ala Lys Thr Asp His Gly Ala Glu Ile Val Tyr Lys Ser
                325                 330                 335

Pro Val Val Ser Gly Asp Thr Ser Pro Arg His Leu Ser Asn Val Ser
            340                 345                 350

Ser Thr Gly Ser Ile Asp Met Val Asp Ser Pro Gln Leu Ala Thr Leu
        355                 360                 365

Ala Asp Glu Val Ser Ala Ser Leu Ala Lys Gln Gly Leu
            370                 375                 380

<210> SEQ ID NO 7
<211> LENGTH: 410
<212> TYPE: PRT
<213> ORGANISM: Homo sapiens
<300> PUBLICATION INFORMATION:
<308> DATABASE ACCESSION NUMBER: Uniprot
<309> DATABASE ENTRY DATE: 2011-05-31
<313> RELEVANT RESIDUES IN SEQ ID NO: (1)..(410)

<400> SEQUENCE: 7

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Glu Ser Pro Leu
        35                  40                  45

Gln Thr Pro Thr Glu Asp Gly Ser Glu Glu Pro Gly Ser Glu Thr Ser
    50                  55                  60

Asp Ala Lys Ser Thr Pro Thr Ala Glu Asp Val Thr Ala Pro Leu Val
65                  70                  75                  80

Asp Glu Gly Ala Pro Gly Lys Gln Ala Ala Ala Gln Pro His Thr Glu
                85                  90                  95

Ile Pro Glu Gly Thr Thr Ala Glu Ala Gly Ile Gly Asp Thr Pro
            100                 105                 110

Ser Leu Glu Asp Glu Ala Ala Gly His Val Thr Gln Ala Arg Met Val
        115                 120                 125

Ser Lys Ser Lys Asp Gly Thr Gly Ser Asp Asp Lys Lys Ala Lys Gly
    130                 135                 140

Ala Asp Gly Lys Thr Lys Ile Ala Thr Pro Arg Gly Ala Ala Pro Pro
145                 150                 155                 160

Gly Gln Lys Gly Gln Ala Asn Ala Thr Arg Ile Pro Ala Lys Thr Pro
                165                 170                 175

Pro Ala Pro Lys Thr Pro Pro Ser Ser Gly Glu Pro Pro Lys Ser Gly
            180                 185                 190

Asp Arg Ser Gly Tyr Ser Ser Pro Gly Ser Pro Gly Thr Pro Gly Ser
        195                 200                 205

Arg Ser Arg Thr Pro Ser Leu Pro Thr Pro Pro Thr Arg Glu Pro Lys
    210                 215                 220

Lys Val Ala Val Val Arg Thr Pro Pro Lys Ser Pro Ser Ser Ala Lys
225                 230                 235                 240
```

```
Ser Arg Leu Gln Thr Ala Pro Val Pro Met Pro Asp Leu Lys Asn Val
            245                 250                 255

Lys Ser Lys Ile Gly Ser Thr Glu Asn Leu Lys His Gln Pro Gly Gly
            260                 265                 270

Gly Lys Val Gln Ile Val Tyr Lys Pro Val Asp Leu Ser Lys Val Thr
            275                 280                 285

Ser Lys Cys Gly Ser Leu Gly Asn Ile His His Lys Pro Gly Gly Gly
            290                 295                 300

Gln Val Glu Val Lys Ser Glu Lys Leu Asp Phe Lys Asp Arg Val Gln
305                 310                 315                 320

Ser Lys Ile Gly Ser Leu Asp Asn Ile Thr His Val Pro Gly Gly Gly
            325                 330                 335

Asn Lys Lys Ile Glu Thr His Lys Leu Thr Phe Arg Glu Asn Ala Lys
            340                 345                 350

Ala Lys Thr Asp His Gly Ala Glu Ile Val Tyr Lys Ser Pro Val Val
            355                 360                 365

Ser Gly Asp Thr Ser Pro Arg His Leu Ser Asn Val Ser Ser Thr Gly
            370                 375                 380

Ser Ile Asp Met Val Asp Ser Pro Gln Leu Ala Thr Leu Ala Asp Glu
385                 390                 395                 400

Val Ser Ala Ser Leu Ala Lys Gln Gly Leu
            405                 410

<210> SEQ ID NO 8
<211> LENGTH: 383
<212> TYPE: PRT
<213> ORGANISM: Homo sapiens
<300> PUBLICATION INFORMATION:
<308> DATABASE ACCESSION NUMBER: Uniprot
<309> DATABASE ENTRY DATE: 2011-05-31
<313> RELEVANT RESIDUES IN SEQ ID NO: (1)..(383)

<400> SEQUENCE: 8

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Ala Glu Glu Ala
            35                  40                  45

Gly Ile Gly Asp Thr Pro Ser Leu Glu Asp Glu Ala Ala Gly His Val
        50                  55                  60

Thr Gln Ala Arg Met Val Ser Lys Ser Lys Asp Gly Thr Gly Ser Asp
65                  70                  75                  80

Asp Lys Lys Ala Lys Gly Ala Asp Gly Lys Thr Lys Ile Ala Thr Pro
            85                  90                  95

Arg Gly Ala Ala Pro Pro Gly Gln Lys Gly Gln Ala Asn Ala Thr Arg
            100                 105                 110

Ile Pro Ala Lys Thr Pro Pro Ala Pro Lys Thr Pro Pro Ser Ser Gly
            115                 120                 125

Glu Pro Pro Lys Ser Gly Asp Arg Ser Gly Tyr Ser Ser Pro Gly Ser
            130                 135                 140

Pro Gly Thr Pro Gly Ser Arg Ser Arg Thr Pro Ser Leu Pro Thr Pro
145                 150                 155                 160

Pro Thr Arg Glu Pro Lys Lys Val Ala Val Val Arg Thr Pro Pro Lys
            165                 170                 175
```

-continued

```
Ser Pro Ser Ser Ala Lys Ser Arg Leu Gln Thr Ala Pro Val Pro Met
            180                 185                 190

Pro Asp Leu Lys Asn Val Lys Ser Lys Ile Gly Ser Thr Glu Asn Leu
        195                 200                 205

Lys His Gln Pro Gly Gly Gly Lys Val Gln Ile Ile Asn Lys Lys Leu
    210                 215                 220

Asp Leu Ser Asn Val Gln Ser Lys Cys Gly Ser Lys Asp Asn Ile Lys
225                 230                 235                 240

His Val Pro Gly Gly Gly Ser Val Gln Ile Val Tyr Lys Pro Val Asp
                245                 250                 255

Leu Ser Lys Val Thr Ser Lys Cys Gly Ser Leu Gly Asn Ile His His
            260                 265                 270

Lys Pro Gly Gly Gly Gln Val Glu Val Lys Ser Glu Lys Leu Asp Phe
        275                 280                 285

Lys Asp Arg Val Gln Ser Lys Ile Gly Ser Leu Asp Asn Ile Thr His
    290                 295                 300

Val Pro Gly Gly Gly Asn Lys Lys Ile Glu Thr His Lys Leu Thr Phe
305                 310                 315                 320

Arg Glu Asn Ala Lys Ala Lys Thr Asp His Gly Ala Glu Ile Val Tyr
                325                 330                 335

Lys Ser Pro Val Val Ser Gly Asp Thr Ser Pro Arg His Leu Ser Asn
            340                 345                 350

Val Ser Ser Thr Gly Ser Ile Asp Met Val Asp Ser Pro Gln Leu Ala
        355                 360                 365

Thr Leu Ala Asp Glu Val Ser Ala Ser Leu Ala Lys Gln Gly Leu
    370                 375                 380

<210> SEQ ID NO 9
<211> LENGTH: 412
<212> TYPE: PRT
<213> ORGANISM: Homo sapiens
<300> PUBLICATION INFORMATION:
<308> DATABASE ACCESSION NUMBER: Uniprot
<309> DATABASE ENTRY DATE: 2011-05-31
<313> RELEVANT RESIDUES IN SEQ ID NO: (1)..(412)

<400> SEQUENCE: 9

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Glu Ser Pro Leu
        35                  40                  45

Gln Thr Pro Thr Glu Asp Gly Ser Glu Glu Pro Gly Ser Glu Thr Ser
    50                  55                  60

Asp Ala Lys Ser Thr Pro Thr Ala Glu Ala Glu Glu Ala Gly Ile Gly
65                  70                  75                  80

Asp Thr Pro Ser Leu Glu Asp Glu Ala Ala Gly His Val Thr Gln Ala
                85                  90                  95

Arg Met Val Ser Lys Ser Lys Asp Gly Thr Gly Ser Asp Asp Lys Lys
            100                 105                 110

Ala Lys Gly Ala Asp Gly Lys Thr Lys Ile Ala Thr Pro Arg Gly Ala
        115                 120                 125

Ala Pro Pro Gly Gln Lys Gly Gln Ala Asn Ala Thr Arg Ile Pro Ala
    130                 135                 140

Lys Thr Pro Pro Ala Pro Lys Thr Pro Pro Ser Ser Gly Glu Pro Pro
```

```
145                 150                 155                 160
Lys Ser Gly Asp Arg Ser Gly Tyr Ser Ser Pro Gly Ser Pro Gly Thr
                165                 170                 175

Pro Gly Ser Arg Ser Arg Thr Pro Ser Leu Pro Thr Pro Pro Thr Arg
                180                 185                 190

Glu Pro Lys Lys Val Ala Val Val Arg Thr Pro Pro Lys Ser Pro Ser
                195                 200                 205

Ser Ala Lys Ser Arg Leu Gln Thr Ala Pro Val Pro Met Pro Asp Leu
            210                 215                 220

Lys Asn Val Lys Ser Lys Ile Gly Ser Thr Glu Asn Leu Lys His Gln
225                 230                 235                 240

Pro Gly Gly Gly Lys Val Gln Ile Ile Asn Lys Lys Leu Asp Leu Ser
                245                 250                 255

Asn Val Gln Ser Lys Cys Gly Ser Lys Asp Asn Ile Lys His Val Pro
                260                 265                 270

Gly Gly Gly Ser Val Gln Ile Val Tyr Lys Pro Val Asp Leu Ser Lys
                275                 280                 285

Val Thr Ser Lys Cys Gly Ser Leu Gly Asn Ile His His Lys Pro Gly
            290                 295                 300

Gly Gly Gln Val Glu Val Lys Ser Glu Lys Leu Asp Phe Lys Asp Arg
305                 310                 315                 320

Val Gln Ser Lys Ile Gly Ser Leu Asp Asn Ile Thr His Val Pro Gly
                325                 330                 335

Gly Gly Asn Lys Lys Ile Glu Thr His Lys Leu Thr Phe Arg Glu Asn
                340                 345                 350

Ala Lys Ala Lys Thr Asp His Gly Ala Glu Ile Val Tyr Lys Ser Pro
            355                 360                 365

Val Val Ser Gly Asp Thr Ser Pro Arg His Leu Ser Asn Val Ser Ser
            370                 375                 380

Thr Gly Ser Ile Asp Met Val Asp Ser Pro Gln Leu Ala Thr Leu Ala
385                 390                 395                 400

Asp Glu Val Ser Ala Ser Leu Ala Lys Gln Gly Leu
                405                 410

<210> SEQ ID NO 10
<211> LENGTH: 441
<212> TYPE: PRT
<213> ORGANISM: Homo sapiens
<300> PUBLICATION INFORMATION:
<308> DATABASE ACCESSION NUMBER: Uniprot
<309> DATABASE ENTRY DATE: 2011-05-31
<313> RELEVANT RESIDUES IN SEQ ID NO: (1)..(441)

<400> SEQUENCE: 10

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
                20                  25                  30

Gln Asp Gln Glu Gly Asp Thr Asp Ala Gly Leu Lys Glu Ser Pro Leu
            35                  40                  45

Gln Thr Pro Thr Glu Asp Gly Ser Glu Glu Pro Gly Ser Glu Thr Ser
        50                  55                  60

Asp Ala Lys Ser Thr Pro Thr Ala Glu Asp Val Thr Ala Pro Leu Val
65                  70                  75                  80

Asp Glu Gly Ala Pro Gly Lys Gln Ala Ala Ala Gln Pro His Thr Glu
                85                  90                  95
```

```
Ile Pro Glu Gly Thr Thr Ala Glu Glu Ala Gly Ile Gly Asp Thr Pro
            100                 105                 110

Ser Leu Glu Asp Glu Ala Ala Gly His Val Thr Gln Ala Arg Met Val
            115                 120                 125

Ser Lys Ser Lys Asp Gly Thr Gly Ser Asp Asp Lys Lys Ala Lys Gly
        130                 135                 140

Ala Asp Gly Lys Thr Lys Ile Ala Thr Pro Arg Gly Ala Ala Pro Pro
145                 150                 155                 160

Gly Gln Lys Gly Gln Ala Asn Ala Thr Arg Ile Pro Ala Lys Thr Pro
                165                 170                 175

Pro Ala Pro Lys Thr Pro Pro Ser Ser Gly Glu Pro Pro Lys Ser Gly
            180                 185                 190

Asp Arg Ser Gly Tyr Ser Ser Pro Gly Ser Pro Gly Thr Pro Gly Ser
            195                 200                 205

Arg Ser Arg Thr Pro Ser Leu Pro Thr Pro Pro Thr Arg Glu Pro Lys
        210                 215                 220

Lys Val Ala Val Val Arg Thr Pro Pro Lys Ser Pro Ser Ser Ala Lys
225                 230                 235                 240

Ser Arg Leu Gln Thr Ala Pro Val Pro Met Pro Asp Leu Lys Asn Val
                245                 250                 255

Lys Ser Lys Ile Gly Ser Thr Glu Asn Leu Lys His Gln Pro Gly Gly
            260                 265                 270

Gly Lys Val Gln Ile Ile Asn Lys Lys Leu Asp Leu Ser Asn Val Gln
            275                 280                 285

Ser Lys Cys Gly Ser Lys Asp Asn Ile Lys His Val Pro Gly Gly Gly
        290                 295                 300

Ser Val Gln Ile Val Tyr Lys Pro Val Asp Leu Ser Lys Val Thr Ser
305                 310                 315                 320

Lys Cys Gly Ser Leu Gly Asn Ile His His Lys Pro Gly Gly Gly Gln
                325                 330                 335

Val Glu Val Lys Ser Glu Lys Leu Asp Phe Lys Asp Arg Val Gln Ser
            340                 345                 350

Lys Ile Gly Ser Leu Asp Asn Ile Thr His Val Pro Gly Gly Gly Asn
            355                 360                 365

Lys Lys Ile Glu Thr His Lys Leu Thr Phe Arg Glu Asn Ala Lys Ala
        370                 375                 380

Lys Thr Asp His Gly Ala Glu Ile Val Tyr Lys Ser Pro Val Val Ser
385                 390                 395                 400

Gly Asp Thr Ser Pro Arg His Leu Ser Asn Val Ser Ser Thr Gly Ser
                405                 410                 415

Ile Asp Met Val Asp Ser Pro Gln Leu Ala Thr Leu Ala Asp Glu Val
            420                 425                 430

Ser Ala Ser Leu Ala Lys Gln Gly Leu
        435                 440

<210> SEQ ID NO 11
<211> LENGTH: 442
<212> TYPE: PRT
<213> ORGANISM: Mus musculus
<300> PUBLICATION INFORMATION:
<308> DATABASE ACCESSION NUMBER: ChEMBL
<309> DATABASE ENTRY DATE: 2015-01-14
<313> RELEVANT RESIDUES IN SEQ ID NO: (1)..(442)

<400> SEQUENCE: 11
```

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Ser Met Ser Trp Val Arg Gln Ala Pro Gly Lys Gly Leu Glu Leu Val
        35                  40                  45

Ala Gln Ile Asn Ser Val Gly Asn Ser Thr Tyr Tyr Pro Asp Thr Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ser Gly Asp Tyr Trp Gly Gln Gly Thr Leu Val Thr Val Ser Ser
            100                 105                 110

Ala Ser Thr Lys Gly Pro Ser Val Phe Pro Leu Ala Pro Ser Ser Lys
        115                 120                 125

Ser Thr Ser Gly Gly Thr Ala Ala Leu Gly Cys Leu Val Lys Asp Tyr
    130                 135                 140

Phe Pro Glu Pro Val Thr Val Ser Trp Asn Ser Gly Ala Leu Thr Ser
145                 150                 155                 160

Gly Val His Thr Phe Pro Ala Val Leu Gln Ser Ser Gly Leu Tyr Ser
                165                 170                 175

Leu Ser Ser Val Val Thr Val Pro Ser Ser Leu Gly Thr Gln Thr
            180                 185                 190

Tyr Ile Cys Asn Val Asn His Lys Pro Ser Asn Thr Lys Val Asp Lys
        195                 200                 205

Lys Val Glu Pro Lys Ser Cys Asp Lys Thr His Thr Cys Pro Pro Cys
    210                 215                 220

Pro Ala Pro Glu Leu Leu Gly Gly Pro Ser Val Phe Leu Phe Pro Pro
225                 230                 235                 240

Lys Pro Lys Asp Thr Leu Met Ile Ser Arg Thr Pro Glu Val Thr Cys
                245                 250                 255

Val Val Val Asp Val Ser His Glu Asp Pro Glu Val Lys Phe Asn Trp
            260                 265                 270

Tyr Val Asp Gly Val Glu Val His Asn Ala Lys Thr Lys Pro Arg Glu
        275                 280                 285

Glu Gln Tyr Asn Ser Thr Tyr Arg Val Val Ser Val Leu Thr Val Leu
    290                 295                 300

His Gln Asp Trp Leu Asn Gly Lys Glu Tyr Lys Cys Lys Val Ser Asn
305                 310                 315                 320

Lys Ala Leu Pro Ala Pro Ile Glu Lys Thr Ile Ser Lys Ala Lys Gly
                325                 330                 335

Gln Pro Arg Glu Pro Gln Val Tyr Thr Leu Pro Pro Ser Arg Asp Glu
            340                 345                 350

Leu Thr Lys Asn Gln Val Ser Leu Thr Cys Leu Val Lys Gly Phe Tyr
        355                 360                 365

Pro Ser Asp Ile Ala Val Glu Trp Glu Ser Asn Gly Gln Pro Glu Asn
    370                 375                 380

Asn Tyr Lys Thr Thr Pro Pro Val Leu Asp Ser Asp Gly Ser Phe Phe
385                 390                 395                 400

Leu Tyr Ser Lys Leu Thr Val Asp Lys Ser Arg Trp Gln Gln Gly Asn
                405                 410                 415

Val Phe Ser Cys Ser Val Met His Glu Ala Leu His Asn His Tyr Thr
```

```
                       420                 425                 430

Gln Lys Ser Leu Ser Leu Ser Pro Gly Lys
        435                 440

<210> SEQ ID NO 12
<211> LENGTH: 219
<212> TYPE: PRT
<213> ORGANISM: Mus musculus
<300> PUBLICATION INFORMATION:
<308> DATABASE ACCESSION NUMBER: ChEMBLE
<309> DATABASE ENTRY DATE: 2014-01-14
<313> RELEVANT RESIDUES IN SEQ ID NO: (1)..(219)

<400> SEQUENCE: 12

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Ile Tyr Ser
            20                  25                  30

Asp Gly Asn Ala Tyr Leu His Trp Phe Leu Gln Lys Pro Gly Gln Ser
        35                  40                  45

Pro Arg Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Val Pro Trp Thr Phe Gly Gln Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 13
<211> LENGTH: 438
<212> TYPE: PRT
<213> ORGANISM: Mus musculus
<300> PUBLICATION INFORMATION:
<308> DATABASE ACCESSION NUMBER: ChEMBL
<309> DATABASE ENTRY DATE: 2015-01-14
<313> RELEVANT RESIDUES IN SEQ ID NO: (1)..(438)

<400> SEQUENCE: 13

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Gly Met Ser Trp Val Arg Gln Ala Pro Gly Lys Gly Leu Glu Leu Val
        35                  40                  45
```

Ala Ser Ile Asn Ser Asn Gly Gly Ser Thr Tyr Tyr Pro Asp Ser Val
            50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Ser Gly Asp Tyr Trp Gly Gln Gly Thr Thr Val Thr Val Ser Ser
            100                 105                 110

Ala Ser Thr Lys Gly Pro Ser Val Phe Pro Leu Ala Pro Cys Ser Arg
            115                 120                 125

Ser Thr Ser Glu Ser Thr Ala Ala Leu Gly Cys Leu Val Lys Asp Tyr
            130                 135                 140

Phe Pro Glu Pro Val Thr Val Ser Trp Asn Ser Gly Ala Leu Thr Ser
145                 150                 155                 160

Gly Val His Thr Phe Pro Ala Val Leu Gln Ser Ser Gly Leu Tyr Ser
                165                 170                 175

Leu Ser Ser Val Val Thr Val Pro Ser Ser Ser Leu Gly Thr Lys Thr
            180                 185                 190

Tyr Thr Cys Asn Val Asp His Lys Pro Ser Asn Thr Lys Val Asp Lys
            195                 200                 205

Arg Val Glu Ser Lys Tyr Gly Pro Pro Cys Pro Pro Cys Pro Ala Pro
210                 215                 220

Glu Phe Leu Gly Gly Pro Ser Val Phe Leu Phe Pro Pro Lys Pro Lys
225                 230                 235                 240

Asp Thr Leu Met Ile Ser Arg Thr Pro Glu Val Thr Cys Val Val Val
                245                 250                 255

Asp Val Ser Gln Glu Asp Pro Glu Val Gln Phe Asn Trp Tyr Val Asp
            260                 265                 270

Gly Val Glu Val His Asn Ala Lys Thr Lys Pro Arg Glu Glu Gln Phe
            275                 280                 285

Asn Ser Thr Tyr Arg Val Val Ser Val Leu Thr Val Leu His Gln Asp
290                 295                 300

Trp Leu Asn Gly Lys Glu Tyr Lys Cys Lys Val Ser Asn Lys Gly Leu
305                 310                 315                 320

Pro Ser Ser Ile Glu Lys Thr Ile Ser Lys Ala Lys Gly Gln Pro Arg
                325                 330                 335

Glu Pro Gln Val Tyr Thr Leu Pro Pro Ser Gln Glu Glu Met Thr Lys
            340                 345                 350

Asn Gln Val Ser Leu Thr Cys Leu Val Lys Gly Phe Tyr Pro Ser Asp
            355                 360                 365

Ile Ala Val Glu Trp Glu Ser Asn Gly Gln Pro Glu Asn Asn Tyr Lys
            370                 375                 380

Thr Thr Pro Pro Val Leu Asp Ser Asp Gly Ser Phe Phe Leu Tyr Ser
385                 390                 395                 400

Arg Leu Thr Val Asp Lys Ser Arg Trp Gln Glu Gly Asn Val Phe Ser
                405                 410                 415

Cys Ser Val Met His Glu Ala Leu His Asn His Tyr Thr Gln Lys Ser
            420                 425                 430

Leu Ser Leu Ser Leu Gly
            435

<210> SEQ ID NO 14
<211> LENGTH: 219

```
<212> TYPE: PRT
<213> ORGANISM: Mus musculus
<300> PUBLICATION INFORMATION:
<308> DATABASE ACCESSION NUMBER: ChEMBL
<309> DATABASE ENTRY DATE: 2015-01-14
<313> RELEVANT RESIDUES IN SEQ ID NO: (1)..(219)

<400> SEQUENCE: 14

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val Tyr Ser
            20                  25                  30

Asn Gly Asp Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Val Pro Trp Thr Phe Gly Gln Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 15
<211> LENGTH: 449
<212> TYPE: PRT
<213> ORGANISM: Mus musculus
<300> PUBLICATION INFORMATION:
<302> TITLE: TREATMENT OF AMYLOIDOGENIC DISEASES WITH HUMANISED
      ANTI-ABETA ANTIBODIES
<310> PATENT DOCUMENT NUMBER: EP2182983
<311> PATENT FILING DATE: 2007-07-27
<312> PUBLICATION DATE: 2014-05-21
<300> PUBLICATION INFORMATION:
<302> TITLE: PREVENTION AND TREATMENT OF CEREBRAL AMYLOID ANGIOPATHY
<310> PATENT DOCUMENT NUMBER: US 20080292625 A1
<311> PATENT FILING DATE: 2008-04-18
<312> PUBLICATION DATE: 2008-11-27

<400> SEQUENCE: 15

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Gly Met Ser Trp Val Arg Gln Ala Pro Gly Lys Gly Leu Glu Trp Val
        35                  40                  45
```

```
Ala Ser Ile Arg Ser Gly Gly Gly Arg Thr Tyr Tyr Ser Asp Asn Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Val Arg Tyr Asp His Tyr Ser Gly Ser Ser Asp Tyr Trp Gly Gln Gly
                100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 16
```

```
<211> LENGTH: 219
<212> TYPE: PRT
<213> ORGANISM: Mus musculus
<300> PUBLICATION INFORMATION:
<302> TITLE: TREATMENT OF AMYLOIDOGENIC DISEASES WITH HUMANISED
      ANTI-ABETA ANTIBODIES
<310> PATENT DOCUMENT NUMBER: EP2182983
<311> PATENT FILING DATE: 2007-07-27
<312> PUBLICATION DATE: 2014-05-21

<400> SEQUENCE: 16

Asp Val Val Met Thr Gln Ser Pro Leu Ser Leu Pro Val Thr Pro Gly
1               5                   10                  15

Glu Pro Ala Ser Ile Ser Cys Lys Ser Gln Ser Leu Leu Asp Ser
            20                  25                  30

Asp Gly Lys Thr Tyr Leu Asn Trp Leu Leu Gln Lys Pro Gly Gln Ser
        35                  40                  45

Pro Gln Arg Leu Ile Tyr Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Thr His Phe Pro Arg Thr Phe Gly Gln Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 17
<211> LENGTH: 124
<212> TYPE: PRT
<213> ORGANISM: Homo sapiens
<300> PUBLICATION INFORMATION:
<302> TITLE: A METHOD OF REDUCING BRAIN AMYLOID PLAQUES USING ANTI-ABeta
      ANTIBODIES
<310> PATENT DOCUMENT NUMBER: WO 2014089500
<311> PATENT FILING DATE: 2013-12-06
<312> PUBLICATION DATE: 2014-06-12

<400> SEQUENCE: 17

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Ala Phe Ser Ser Tyr
            20                  25                  30

Gly Met His Trp Val Arg Gln Ala Pro Gly Lys Gly Leu Glu Trp Val
        35                  40                  45

Ala Val Ile Trp Phe Asp Gly Thr Lys Lys Tyr Tyr Thr Asp Ser Val
    50                  55                  60
```

```
Lys Gly Arg Phe Thr Ile Ser Arg Asp Asn Ser Lys Asn Thr Leu Tyr
 65                  70                  75                  80

Leu Gln Met Asn Thr Leu Arg Ala Glu Asp Thr Ala Val Tyr Tyr Cys
                 85                  90                  95

Ala Arg Asp Arg Gly Ile Gly Ala Arg Arg Gly Pro Tyr Tyr Met Asp
            100                 105                 110

Val Trp Gly Lys Gly Thr Thr Val Thr Val Ser Ser
            115                 120

<210> SEQ ID NO 18
<211> LENGTH: 108
<212> TYPE: PRT
<213> ORGANISM: Homo sapiens
<300> PUBLICATION INFORMATION:
<302> TITLE: A METHOD OF REDUCING BRAIN AMYLOID PLAQUES USING ANTI-ABeta
      ANTIBODIES
<310> PATENT DOCUMENT NUMBER: WO 2014089500
<311> PATENT FILING DATE: 2013-12-06
<312> PUBLICATION DATE: 2014-06-12

<400> SEQUENCE: 18

Asp Ile Gln Met Thr Gln Ser Pro Ser Ser Leu Ser Ala Ser Val Gly
1                5                  10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
                85                  90                  95

Thr Phe Gly Gly Gly Thr Lys Val Glu Ile Lys Arg
            100                 105

<210> SEQ ID NO 19
<211> LENGTH: 112
<212> TYPE: PRT
<213> ORGANISM: Mus musculus
<300> PUBLICATION INFORMATION:
<302> TITLE: AMYLOID-BETA GLOBULOMER ANTIBODIES
<310> PATENT DOCUMENT NUMBER: US 8497072
<311> PATENT FILING DATE: 2008-12-31
<312> PUBLICATION DATE: 2009-09-24

<400> SEQUENCE: 19

Glu Val Gln Leu Val Glu Ser Gly Gly Gly Leu Val Gln Pro Gly Gly
1                5                  10                  15

Ser Leu Lys Leu Ser Cys Ala Ala Ser Gly Phe Thr Phe Ser Ser Tyr
            20                  25                  30

Gly Met Ser Trp Val Arg Gln Thr Pro Asp Lys Arg Leu Glu Leu Val
        35                  40                  45

Ala Ser Ile Asn Ser Asn Gly Gly Ser Thr Tyr Tyr Pro Asp Ser Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Met Tyr Tyr Cys
                85                  90                  95
```

```
Ala Ser Gly Asp Tyr Trp Gly Gln Gly Ser Thr Leu Thr Val Ser Ser
            100                 105                 110

<210> SEQ ID NO 20
<211> LENGTH: 111
<212> TYPE: PRT
<213> ORGANISM: Mus musculus
<300> PUBLICATION INFORMATION:
<302> TITLE: AMYLOID-BETA GLOBULOMER ANTIBODIES
<310> PATENT DOCUMENT NUMBER: US 8497072
<311> PATENT FILING DATE: 2008-12-31
<312> PUBLICATION DATE: 2009-09-24

<400> SEQUENCE: 20

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val Tyr Ser
            20                  25                  30

Asn Gly Asp Thr Tyr Leu His Trp Tyr Leu Gln Lys Pro Gly Gln Ser
            35                  40                  45

Pro Lys Leu Leu Ile Tyr Lys Val Ser Asn Arg Phe Ser Gly Val Pro
        50                  55                  60

Asp Arg Phe Ser Gly Ser Gly Thr Asp Phe Thr Leu Lys Ile Ser Arg
65                  70                  75                  80

Val Glu Ala Glu Asp Leu Gly Val Tyr Phe Cys Ser Gln Ser Thr His
                85                  90                  95

Val Pro Trp Thr Phe Gly Gly Gly Thr Lys Leu Glu Ile Lys Arg
            100                 105                 110
```

DETECTION OF MISFOLDED AMYLOID BETA PROTEIN

CROSS-REFERENCE TO RELATED APPLICATIONS

This application claims priority from U.S. Provisional Patent Application No. 62/049,303, filed on Sep. 11, 2014, the entire contents of which are incorporated herein by reference.

The Sequence Listing submitted as a text file named "Amprion-15US_SequenceListing_ST25.txt" created Mar. 9, 2017, and having a size of 59,259 bytes, is entirely incorporated by reference herein.

BACKGROUND

Protein misfolding disorders (PMDs) include Alzheimer's disease, Parkinson's disease, type 2 diabetes, Huntington's disease, amyotrophic lateral sclerosis, systemic amyloidosis, prion diseases, and the like. Misfolded aggregates of different proteins may be formed and accumulate. The misfolded aggregates may induce cellular dysfunction and tissue damage, among other effects.

For example, Alzheimer's disease (AD) is a degenerative brain disorder with no effective treatment or accurate pre-clinical diagnosis. Evidence to date suggests that the mis-folding, aggregation, and brain deposition of the amyloid-beta protein (Aβ) may be triggering factors for AD pathology. While Aβ plaques were originally thought to be the hallmark of the disease, current research suggests that soluble Aβ oligomers may be critical synapto-toxic species causing neurodegeneration in AD. Because the brain has low regeneration capacity, early diagnosis of AD is crucial to permit intervention before irreversible neuropathological changes occur. Several lines of evidence indicate that the process of Aβ misfolding and oligomerization may begin years or decades before the onset of clinical symptoms and substantial brain damage. Current diagnosis of AD may include clinical examination complemented by imaging techniques used mainly to rule out other forms of dementia. Definitive diagnosis is done post-mortem by histological examination of the brain for the presence of amyloid plaques and neurofibrillary tangles. Still, the lack of a widely accepted early, sensitive, and objective laboratory diagnosis remains a major problem for AD care.

The present application appreciates that diagnosis of AD may be a challenging endeavor.

SUMMARY

In one embodiment, a method for determining a presence of a soluble, misfolded Aβ protein in a sample is provided. The method may include contacting the sample with a monomeric, folded Aβ protein to form an incubation mixture. The method may include conducting an incubation cycle two or more times on the incubation mixture effective to form an amplified portion of misfolded Aβ protein from the monomeric, folded Aβ protein. Each incubation cycle may include incubating the incubation mixture effective to cause misfolding and/or aggregation of at least a portion of the monomeric, folded Aβ protein in the presence of the soluble, misfolded Aβ protein. Each incubation cycle may include physically disrupting the incubation mixture effective to at least partly de-aggregate at least a portion of a misfolded Aβ aggregate present. The method may include determining the presence of the soluble, misfolded Aβ protein in the sample by detecting at least a portion of the amplified portion of misfolded Aβ protein. The soluble, misfolded Aβ protein may include one or more of: a soluble, misfolded Aβ monomer and a soluble, misfolded Aβ aggregate. The amplified portion of misfolded Aβ protein may include one or more of: an amplified portion of the soluble, misfolded Aβ monomer, an amplified portion of the soluble, misfolded Aβ aggregate, and an insoluble, misfolded Aβ aggregate.

In another embodiment, a method for determining a presence of a soluble, misfolded Aβ protein in a sample is provided. The method may include contacting the sample with Thioflavin T and a monomeric, folded Aβ protein to form an incubation mixture. The method may include conducting an incubation cycle two or more times on the incubation mixture effective to form an amplified portion of misfolded Aβ protein from the monomeric, folded Aβ protein. Each incubation cycle may include incubating the incubation mixture effective to cause misfolding and/or aggregation of at least a portion of the monomeric, folded Aβ protein in the presence of the soluble, misfolded Aβ protein. Each incubation cycle may include shaking the incubation mixture effective to at least partly de-aggregate at least a portion of a misfolded Aβ aggregate present. The method may include determining the presence of the soluble, misfolded Aβ protein in the sample by detecting a fluorescence of the Thioflavin T corresponding to at least a portion of the amplified portion of misfolded Aβ protein. The soluble, misfolded Aβ protein may include one or more of: a soluble, misfolded Aβ monomer and a soluble, misfolded Aβ aggregate. The amplified portion of misfolded Aβ protein may include one or more of: an amplified portion of the soluble, misfolded Aβ monomer, an amplified portion of the soluble, misfolded Aβ aggregate, and an insoluble, misfolded Aβ aggregate.

In one embodiment, a method for determining a presence of a soluble, misfolded Aβ protein in a sample is provided. The method may include capturing a soluble, misfolded Aβ protein from the sample to form a captured soluble, misfolded Aβ protein. The method may include contacting the captured, soluble misfolded Aβ protein with a molar excess of monomeric, folded Aβ protein to form an incubation mixture. The molar excess may be greater than an amount of Aβ protein monomer included in the captured soluble, misfolded Aβ protein. The method may include conducting an incubation cycle two or more times on the incubation mixture effective to form an amplified portion of misfolded Aβ protein from the monomeric, folded Aβ protein. Each incubation cycle may include incubating the incubation mixture effective to cause misfolding and/or aggregation of at least a portion of the monomeric, folded Aβ protein in the presence of the captured soluble, misfolded Aβ protein. Each incubation cycle may include physically disrupting the incubation mixture effective to at least partly de-aggregate at least a portion of a misfolded Aβ aggregate present. The method may include determining the presence of the soluble, misfolded Aβ protein in the sample by detecting at least a portion of the amplified portion of misfolded Aβ protein. The soluble, misfolded Aβ protein may include one or more of: a soluble, misfolded Aβ monomer and a soluble, misfolded Aβ aggregate. The captured, soluble, misfolded Aβ protein may include one or more of: a captured, soluble, misfolded Aβ monomer and a captured, soluble, misfolded Aβ aggregate. The amplified portion of misfolded Aβ protein may include one or more of: an amplified portion of the soluble, misfolded Aβ monomer, an amplified portion of the soluble, misfolded Aβ aggregate, and an insoluble, misfolded Aβ aggregate.

In another embodiment, a kit for determining a presence of a soluble, misfolded Aβ protein in a sample is provided. The kit may include one or more of a known amount of a monomeric Aβ protein and a known amount of an indicator of the soluble, misfolded Aβ protein. The kit may include instructions. The instructions may direct a user to contact the sample with one or more of the known amount of the monomeric, folded Aβ protein and the known amount of the indicator of the soluble, misfolded Aβ protein to form an incubation mixture. The instructions may direct a user to conduct an incubation cycle two or more times effective to form an amplified portion of misfolded Aβ protein from the monomeric, folded Aβ protein. Each incubation cycle may include incubating the incubation mixture effective to cause misfolding and/or aggregation of at least a portion of the monomeric, folded Aβ protein in the presence of the soluble, misfolded Aβ protein. Each incubation cycle may include physically disrupting the incubation mixture effective to at least partly de-aggregate at least a portion of a misfolded Aβ aggregate present. The instructions may direct a user to determine the presence of the soluble, misfolded Aβ protein in the sample by detecting at least a portion of the amplified portion of misfolded Aβ protein. The soluble, misfolded Aβ protein may include one or more of: a soluble, misfolded Aβ monomer and a soluble, misfolded Aβ aggregate. The amplified portion of misfolded Aβ protein may include one or more of: an amplified portion of the soluble, misfolded Aβ monomer, an amplified portion of the soluble, misfolded Aβ aggregate, and an insoluble, misfolded Aβ aggregate.

The methods and kits disclosed herein for determining a presence of a soluble, misfolded Aβ protein in a sample may be effective to determine an absence of the soluble, misfolded Aβ protein in the sample.

BRIEF DESCRIPTION OF THE DRAWINGS

The accompanying figures, which are incorporated in and constitute a part of the specification, illustrate example methods and results, and are used merely to illustrate example embodiments.

FIG. 5, Table 1 shows estimations of the sensitivity, specificity and predictive value of the Aβ-PMCA test, calculated using the lag phase numbers.

FIG. 8A is a schematic representation of an ELISA solid phase method employed to capture Aβ oligomers from complex biological samples.

FIG. 8B is a schematic representation of a magnetic bead solid phase method employed to capture Aβ oligomers from complex biological samples.

FIG. 9, Table 2 shows the ability of specific antibodies to capture the Aβ oligomers. The sequence shown at the top of Table 2 corresponds to SEQ ID NO: 3.

DETAILED DESCRIPTION

Figure 1A:
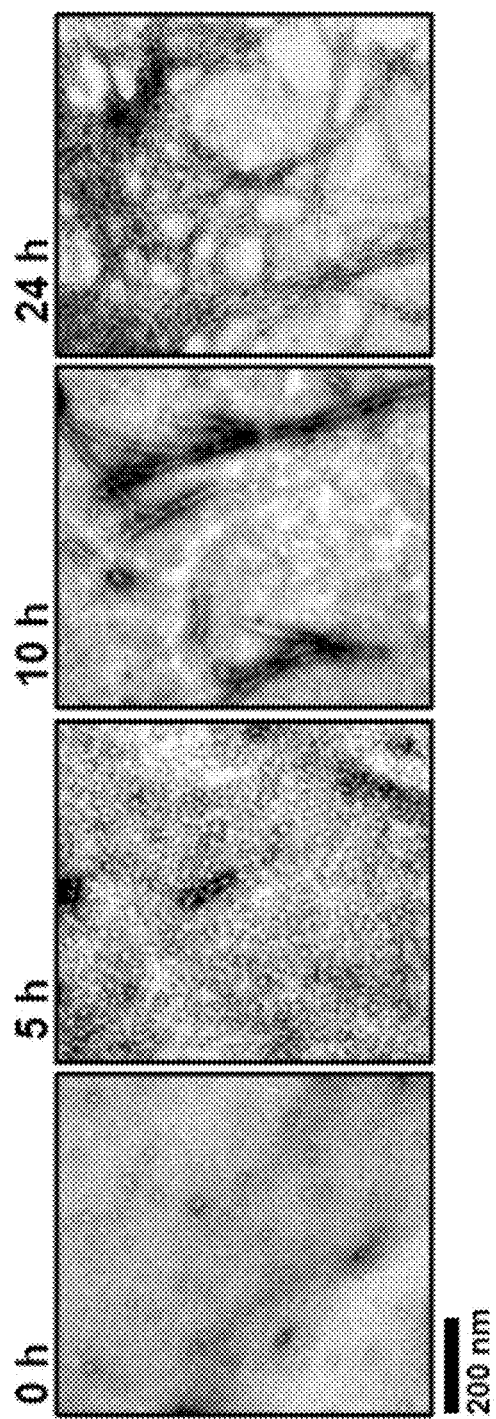
FIG. 1A shows electron micrographs taken at 0 h, 5 h, 10 h, and 24 h of incubation.

Methods and kits are provided for the detection of misfolded proteins, specifically misfolded Aβ in a sample, including for the diagnosis of AD. This process, Protein Misfolding Cyclic Amplification (PMCA), may provide ultra-sensitive detection of misfolded aggregates through artificial acceleration and amplification of the misfolding and aggregation process in vitro. The basic concept of PMCA has been disclosed previously (Soto et al, WO 2002/04954; Estrada, et al. U.S. Pat. App. Pub. No. 20080118938, each of which is entirely incorporated herein by reference). However, prior to the present document, no patent or patent publication has enabled PCMA for the amplification and detection of misfolded Aβ in a sample, including for the diagnosis of AD. This document discloses specific examples and details which enable PMCA technology for the detection of misfolded Aβ proteins, as may be found in AD patients.

In various embodiments, methods and kits for determining a presence of a soluble, misfolded Aβ protein in a sample are provided. As described herein, methods and kits for determining a presence of a soluble, misfolded Aβ protein in a sample may be effective to determine an absence of the soluble, misfolded Aβ protein in the sample. The soluble, misfolded Aβ protein described herein may be a pathogenic protein, e.g., causing or leading to various neural pathologies associated with AD.

The methods may include contacting the sample with a monomeric, folded Aβ protein to form an incubation mixture. The methods may include conducting an incubation cycle two or more times on the incubation mixture effective to form an amplified portion of misfolded Aβ protein from the monomeric, folded Aβ protein. Each incubation cycle may include incubating the incubation mixture effective to cause misfolding and/or aggregation of at least a portion of the monomeric, folded Aβ protein in the presence of the soluble, misfolded Aβ protein. Each incubation cycle may include physically disrupting the incubation mixture effective to at least partly de-aggregate at least a portion of a misfolded Aβ aggregate present. The methods may include determining the presence of the soluble, misfolded Aβ protein in the sample by detecting at least a portion of the amplified portion of misfolded Aβ protein. The soluble, misfolded Aβ protein may include one or more of: a soluble, misfolded Aβ monomer and a soluble, misfolded Aβ aggregate. The amplified portion of misfolded Aβ protein may include one or more of: an amplified portion of the soluble, misfolded Aβ monomer, an amplified portion of the soluble, misfolded Aβ aggregate, and an insoluble, misfolded Aβ aggregate.

As used herein, "Aβ" or "beta amyloid" refers to a peptide formed via sequential cleavage of the amyloid precursor protein (APP) (SEQ ID NO: 1). Various Aβ isoforms may include 38-43 amino acid residues. The Aβ protein may be formed when APP (SEQ ID NO: 1) is processed by β- and/or γ-secretases in any combination. The Aβ may be a constituent of amyloid plaques in brains of individuals suffering from or suspected of having AD. Various Aβ isoforms may include and are not limited to Abeta40 (SEQ ID NO: 2) and Abeta42 (SEQ ID NO: 3). Various Aβ peptides may be associated with neuronal damage associated with AD.

As used herein, "tau" refers to proteins are the product of alternative splicing from a single gene, e.g., MAPT (microtubule-associated protein tau) (SEQ ID NO: 4) in humans. Tau proteins include to full-length and truncated forms of any of tau's isoforms (see SEQ ID NO: 5, SEQ ID NO: 6, SEQ ID NO: 7, SEQ ID NO: 8, SEQ ID NO: 9, and SEQ ID NO: 10). Various isoforms include, but are not limited to, the six tau isoforms known to exist in human brain tissue, which correspond to alternative splicing in exons 2, 3, and 10 of the tau gene. Three isoforms have three binding domains and the other three have four binding domains. Misfolded tau may be present in brains of individuals suffering from AD or suspected of having AD, or other tauopathies.

As used herein, "monomeric, folded Aβ protein" refers to single Aβ protein molecules in their native, nonpathogenic, folded configuration. "Soluble, misfolded Aβ protein" refers to misfolded monomers or aggregates of Aβ protein that remain in solution. Examples of soluble, misfolded Aβ protein may include any number of aggregated misfolded Aβ protein monomers so long as the misfolded Aβ protein remains soluble. For example, soluble, misfolded Aβ protein may include aggregates of between 2 and about 50 units of misfolded Aβ protein monomer. In some examples, aggregates may be referred to as oligomers or polymers. In some examples, aggregation may be referred to as oligomerization or polymerization.

Soluble, misfolded Aβ protein may aggregate or oligomerize to form insoluble aggregates and/or higher oligomers, leading to Aβ protein aggregates in the form of protofibrils, fibrils, and eventually amyloid plaques. "Seeds" or "nuclei" refer to misfolded Aβ protein or short fragmented fibrils, particularly soluble, misfolded Aβ protein, with catalytic activity for inducing further misfolding, oligomerization, and/or aggregation. Such nucleation-dependent polymerization may be characterized by a slow lag phase wherein aggregated nuclei may form, which may then catalyze rapid formation of further and/or larger aggregates. The lag phase may be minimized or removed by addition of pre-formed nuclei or seeds. In some examples, "seeds" or "nuclei" may exclude unaggregated monomers of Aβ protein. Without wishing to be bound by theory, it is believed that at least under some conditions, monomeric, misfolded Aβ protein may not be stable, and the minimum stable size of pathogenic, misfolded Aβ protein may be an aggregate of two monomer units of misfolded Aβ protein.

As used herein, "soluble" species may form a solution in biological fluids under physiological conditions, whereas "insoluble" species may be present as precipitates, fibrils, deposits, tangles, or other non-dissolved forms in such biological fluids under physiological conditions. Such biological fluids may include, for example fluids, or fluids expressed from one or more of: amniotic fluid; bile; blood; cerebrospinal fluid; cerumen; skin; exudate; feces; gastric fluid; lymph; milk; mucus, e.g. nasal secretions; mucosal membrane, e.g., nasal mucosal membrane; peritoneal fluid; plasma; pleural fluid; pus; saliva; sebum; semen; sweat; synovial fluid; tears; urine; and the like. Insoluble species may include, for example, fibrils of Aβ, αS, tau, and the like. A species that dissolves in a nonbiological fluid but not one of the aforementioned biological fluids under physiological conditions is considered insoluble, for example, the insoluble fibrils of Aβ and/or tau, and the like may be dissolved in a solution of, e.g., SDS in water, but are still considered insoluble species herein.

In some embodiments, the sample may exclude insoluble species of the misfolded proteins such as Aβ and/or tau as a precipitate, fibril, deposit, tangle, plaque, or other form that may be insoluble in one or more of the described biological fluids under physiological conditions.

For example, the sample may exclude αS and tau in fibril form. The sample may exclude misfolded Aβ, αS and/or tau proteins in insoluble form, e.g., the sample may exclude the misfolded Aβ, αS and/or tau proteins as precipitates, fibrils, deposits, tangles, plaques, or other insoluble forms, e.g., in fibril form. The methods described herein may include preparing the sample by excluding the misfolded Aβ and tau proteins in insoluble form, e.g., by excluding from the sample the misfolded Aβ and tau proteins as precipitates, fibrils, deposits, tangles, plaques, or other insoluble forms, e.g., in fibril form. The kits described herein may include instructions directing a user to prepare the sample by excluding from the sample the misfolded Aβ, αS and/or tau proteins as precipitates, fibrils, deposits, tangles, plaques, or other insoluble forms, e.g., in fibril form. The exclusion of such insoluble forms of the described misfolded proteins from the sample may be substantial or complete.

As used herein, aggregates of Aβ protein refer to non-covalent associations of protein including soluble, misfolded Aβ protein. Aggregates of Aβ protein may be "de-aggregated", broken up, or disrupted to release smaller aggregates, e.g., soluble, misfolded Aβ protein and fragmented fibrils. The catalytic activity of a collection of misfolded Aβ protein aggregate seeds may scale, at least in part with the number of seeds in a mixture. Accordingly, disruption of aggregates of Aβ protein in a mixture to release soluble, misfolded Aβ protein and fragmented fibrils seeds may lead to an increase in catalytic activity for aggregation of monomeric Aβ protein.

As used herein, a "misfolded protein" is a protein that no longer contains all or part of the structural conformation of the protein as it exists when involved in its typical, non-pathogenic normal function within a biological system. A misfolded protein may aggregate. A misfolded protein may localize in protein aggregate. A misfolded protein may be a non-functional protein. A misfolded protein may be a pathogenic conformer of the protein. Monomeric, folded Aβ protein compositions may be provided in native, nonpathogenic confirmations without the catalytic activity for misfolding, oligomerization, and aggregation associated with seeds. Monomeric, folded Aβ protein compositions may be provided in seed-free form.

In various embodiments, methods for determining a presence of a soluble, misfolded Aβ protein in a sample are provided. The methods may include contacting the sample with Thioflavin T and a monomeric, folded Aβ protein to form an incubation mixture. The methods may include conducting an incubation cycle two or more times on the incubation mixture effective to form an amplified portion of misfolded Aβ protein from the monomeric, folded Aβ protein. Each incubation cycle may include incubating the incubation mixture effective to cause misfolding and/or aggregation of at least a portion of the monomeric, folded Aβ protein in the presence of the soluble, misfolded Aβ protein. Each incubation cycle may include shaking the incubation mixture effective to at least partly de-aggregate at least a portion of a misfolded Aβ aggregate present. The methods may include determining the presence of the soluble, misfolded Aβ protein in the sample by detecting a fluorescence of the Thioflavin T corresponding to at least a portion of the amplified portion of misfolded Aβ protein. The soluble, misfolded Aβ protein may include one or more of: a soluble, misfolded Aβ monomer and a soluble, misfolded Aβ aggregate. The amplified portion of misfolded Aβ protein may include one or more of: an amplified portion of the soluble, misfolded Aβ monomer, an amplified portion of the soluble, misfolded Aβ aggregate, and an insoluble, misfolded Aβ aggregate.

In various embodiments, methods for determining a presence of a soluble, misfolded Aβ protein in a sample are provided. The methods may include capturing a soluble, misfolded Aβ protein from the sample to form a captured soluble, misfolded Aβ protein. The methods may include contacting the captured, misfolded Aβ protein with a molar excess of monomeric, folded Aβ protein to form an incubation mixture. The molar excess may be greater than an amount of Aβ protein monomer included in the captured soluble, misfolded Aβ protein. The methods may include conducting an incubation cycle two or more times on the incubation mixture effective to form an amplified portion of misfolded Aβ protein from the monomeric, folded Aβ protein. Each incubation cycle may include incubating the incubation mixture effective to cause misfolding and/or aggregation of at least a portion of the monomeric, folded Aβ protein in the presence of the captured soluble, misfolded Aβ protein. Each incubation cycle may include physically disrupting the incubation mixture effective to at least partly de-aggregate at least a portion of a misfolded Aβ aggregate present. The methods may include determining the presence of the soluble, misfolded Aβ protein in the sample by detecting at least a portion of the amplified portion of misfolded Aβ protein. The soluble, misfolded Aβ protein may include one or more of: a soluble, misfolded Aβ monomer and a soluble, misfolded Aβ aggregate. The captured, soluble, misfolded Aβ protein may include one or more of: a captured, soluble, misfolded Aβ monomer and a captured, soluble, misfolded Aβ aggregate. The amplified portion of misfolded Aβ protein may include one or more of: an amplified portion of the soluble, misfolded Aβ monomer, an amplified portion of the soluble, misfolded Aβ aggregate, and an insoluble, misfolded Aβ aggregate.

In some embodiments, the methods may include contacting an indicator of the soluble, misfolded protein to one or both of the incubation mixture or the detection mixture. The indicator of the soluble, misfolded Aβ protein may be characterized by an indicating state in the presence of the soluble, misfolded Aβ protein and a non-indicating state in the absence of the soluble, misfolded Aβ protein. determining the presence of the soluble, misfolded Aβ protein in the sample may include detecting the indicating state of the indicator of the soluble, misfolded Aβ protein in the detection mixture. The indicating state of the indicator and the non-indicating state of the indicator may be characterized by a difference in fluorescence, light absorption or radioactivity depending on the specific indicator. Determining the presence of the soluble, misfolded Aβ protein in the sample may include detecting the difference in these parameters.

In several embodiments, the method may include contacting a molar excess of the indicator of the soluble, misfolded Aβ protein to one or both of the incubation mixture or the detection mixture. The molar excess may be greater than a total molar amount of Aβ protein monomer included in the monomeric Aβ protein and the soluble, misfolded Aβ protein in the one or both of the incubation mixture or the detection mixture.

In various embodiments, the indicator of the soluble, misfolded Aβ protein may include one or more of: Thioflavin T, Congo Red, m-I-Stilbene, Chrysamine G, PIB, BF-227, X-34, TZDM, FDDNP, MeO-X-04, IMPY or NIAD-4, luminescent conjugated polythiophenes, a fusion with a fluorescent protein such as green fluorescent protein and yellow fluorescent protein, derivatives thereof, and the like.

In some embodiments, determining the presence of the soluble, misfolded Aβ protein in the sample may include determining an amount of the soluble misfolded Aβ protein in the sample. The amount of the soluble, misfolded Aβ protein in the sample may be determined compared to a control sample. The amount of the soluble, misfolded Aβ protein in the sample may be detected with a sensitivity of at least about one or more of: 80%, 81%, 82%, 83%, 84%, 85%, 86%, 87%, 88%, 89%, 90%, 91%, 92%, 93%, 94%, 95%, 96%, 97%, 98%, 99%, and 100%. The amount of the soluble, misfolded Aβ protein in the sample detected may be less than about one or more of: 100 nmol, 10 nmol, 1 nmol, 100 pmol, 10 pmol, 1 pmol, 100 fmol, 10 fmol, 3 fmol, 1 fmol, 100 attomol, 10 attomol, and 1 attomol. The amount of the soluble, misfolded Aβ protein in the sample may be detected in a molar ratio to monomeric Aβ protein comprised by the sample. The molar ratio may be less than about one or more of 1:100, 1:10,000, 1:100,000, and 1:1,000,000.

In various embodiments, the soluble, misfolded Aβ protein in the sample may be detected with a specificity of at least about one or more of: 80%, 81%, 82%, 83%, 84%, 85%, 86%, 87%, 88%, 89%, 90%, 91%, 92%, 93%, 94%, 95%, 96%, 97%, 98%, 99%, and 100%.

In some embodiments, the incubation mixture may include the monomeric Aβ protein in a concentration, or in a concentration range, of one or more of: between about 1 nM and about 2 mM; between about 10 nM and about 200 μM; between about 100 nM and about 20 μM; or between about 1 μM and about 10 μM; and about 2 μM.

In several embodiments, the incubation mixture may include a buffer composition. The buffer composition may be effective to prepare or maintain the pH of the incubation mixture as described herein, e.g., between pH 5 and pH 9. The buffer composition may include one or more of: Tris-HCL, PBS, MES, PIPES, MOPS, BES, TES, or HEPES, and the like. The buffer concentration may be at a total concentration of between about 1 m and about 1M. For example, the buffer may be Tris-HCL at a concentration of 0.1 M.

In various embodiments, the incubation mixture may include a salt composition. The salt composition may be effective to increase the ionic strength of the incubation mixture. The salt composition may include one or more of: NaCl or KCl, and the like. The incubation mixture may include the salt composition at a total concentration of between about 1 m and about 500 mM.

In several embodiments, the incubation mixture may be characterized by, prepared with, or maintained at a pH value of or a pH range of one or more of: between about 5 and about 9; between about 6 and about 8.5; between about 7 and about 8; and about 7.4.

In some embodiments, the incubation mixture may be incubated at a temperature in ° C. of about one or more of 4, 6, 8, 10, 12, 14, 16, 18, 20, 22, 24, 26, 28, 30, 32, 34, 35, 36, 37, 40, 45, 50, 55, and 60, e.g., about 22° C., or a temperature range between any two of the preceding values, for example, one or more of: between about 4° C. and about 60° C.; between about 4° C. and about 35° C.; between about 8° C. and about 50° C.; between about 12° C. and about 40° C.; between about 18° C. and about 30° C.; between about 18° C. and about 26° C.; and the like.

In several embodiments, the detecting the soluble, misfolded Aβ protein in the detection mixture may include one or more of: a Western Blot assay, a dot blot assay, an enzyme-linked immunosorbent assay (ELISA), a thioflavin T binding assay, a Congo Red binding assay, a sedimentation assay, electron microscopy, atomic force microscopy, surface plasmon resonance, spectroscopy, and the like. The ELISA may include a two-sided sandwich ELISA. The spectroscopy may include one or more of: quasi-light scattering spectroscopy, multispectral ultraviolet spectroscopy, confocal dual-color fluorescence correlation spectroscopy, Fourier-transform infrared spectroscopy, capillary electrophoresis with spectroscopic detection, electron spin resonance spectroscopy, nuclear magnetic resonance spectroscopy, Fluorescence Resonance Energy Transfer (FRET) spectroscopy, and the like.

In various embodiments, the detecting the soluble, misfolded Aβ protein in the detection mixture may include contacting the detection mixture with a protease. The soluble, misfolded Aβ protein may be detected in the detection mixture using sequence-based or anti-misfolded protein antibodies in one or more of: a Western Blot assay, a dot blot assay, and an ELISA.

In some embodiments, the method may include providing the monomeric Aβ protein in labeled form. The monomeric Aβ protein in labeled form may include one or more of: a covalently incorporated radioactive amino acid, a covalently incorporated, isotopically labeled amino acid, and a covalently incorporated fluorophore. The detecting the soluble, misfolded Aβ protein in the detection mixture may include detecting the monomeric Aβ protein in labeled form as incorporated into the amplified portion of the soluble, misfolded Aβ protein.

In several embodiments, the sample may be taken from a subject. The method may include determining or diagnosing the presence of AD in the subject according to the presence of the soluble, misfolded Aβ protein in the sample. The presence of the soluble, misfolded Aβ protein in the sample may be determined compared to a control sample taken from a control subject.

In various embodiments, the detecting may include detecting an amount of the soluble, misfolded Aβ protein in the sample. The method may include determining or diagnosing the presence of AD in the subject by comparing the amount of the soluble, misfolded Aβ protein in the sample to a predetermined threshold amount.

In several embodiments, the sample may be taken from a subject exhibiting no clinical signs of dementia according to cognitive testing. The method may include determining or diagnosing the presence of AD in the subject according to the presence of the soluble, misfolded Aβ protein in the sample.

In some embodiments, the sample may be taken from a subject exhibiting no cortex plaques or tangles according to amyloid beta contrast imaging. The method may further include determining or diagnosing the presence of AD in the subject according to the presence of the soluble, misfolded Aβ protein in the sample.

In various embodiments, the sample may be taken from a subject exhibiting clinical signs of dementia according to cognitive testing. The method may further include determining or diagnosing the presence of AD as a contributing factor to the clinical signs of dementia in the subject according to the presence of the soluble, misfolded Aβ protein in the sample.

In some embodiments, the sample may include one or more of: amniotic fluid; bile; blood; cerebrospinal fluid; cerumen; skin; exudate; feces; gastric fluid; lymph; milk; mucus, e.g. nasal secretions; mucosal membrane, e.g., nasal mucosal membrane; peritoneal fluid; plasma; pleural fluid; pus; saliva; sebum; semen; sweat; synovial fluid; tears; and urine.

In several embodiments, the method may include taking the sample from the subject. The subject may be one of a: human, mouse, rat, dog, cat, cattle, horse, deer, elk, sheep, goat, pig, or non-human primate. Non-human animals may be wild or domesticated. The subject may be one or more of: at risk of AD, having AD, and under treatment for AD, at risk of having a disease associated with dysregulation, misfolding, aggregation or disposition of Aβ, having a disease associated with dysregulation, misfolding, aggregation or disposition of Aβ, or under treatment for a disease associated with dysregulation, misfolding, aggregation or disposition of Aβ.

In various embodiments, the method may include determining or diagnosing a progression or homeostasis of AD in the subject by comparing the amount of the soluble, misfolded Aβ protein in the sample to an amount of the soluble, misfolded Aβ protein in a comparison sample taken from the subject at a different time compared to the sample.

For example, several novel therapeutics that are targeting Aβ homeostasis through various mechanisms are currently under development. A PMCA assay for Aβ oligomers may be employed to determine which patients may be treated with an Aβ modulating therapy. Patients showing a change, e.g., decrease or increase, in the level of Aβ oligomers as detected by the PMCA method may be classified as "responders" to Aβ modulating therapy, and may be treated with a therapeutic reducing the levels of Aβ oligomers. Patients lacking an aberrant Aβ homeostasis may be classified as "non responders" and may not be treated. Patients who could benefit from therapies aimed at modulating Aβ homeostasis may thus be identified.

Further, for example, the amount of Aβ oligomers may be measured in samples from patients using PMCA. Patients with elevated Aβ measurements may be treated with therapeutics modulating Aβ homeostasis. Patients with normal Aβ measurements may not be treated. A response of a patient to therapies aimed at modulating Aβ homeostasis may be followed. For example, Aβ oligomer levels may be measured in a patient sample at the beginning of a therapeutic intervention. Following treatment of the patient for a clinical meaningful period of time, another patient sample may be obtained and Aβ oligomer levels may be measured. Patients who show a change in Aβ levels following therapeutic intervention may be considered to respond to the treatment. Patients who show unchanged Aβ levels may be considered non-responding. The methods may include detection of Aβ aggregates in patient samples containing components that may interfere with the PMCA reaction.

In some embodiments, the subject may be treated with an Aβ modulating therapy. The method may include comparing the amount of the soluble, misfolded Aβ protein in the sample to an amount of the soluble, misfolded Aβ protein in a comparison sample. The sample and the comparison sample may be taken from the subject at different times over a period of time under the Aβ modulating therapy. The method may include determining or diagnosing the subject is one of: responsive to the Aβ modulating therapy according to a change in the soluble, misfolded Aβ protein over the period of time, or non-responsive to the Aβ modulating therapy according to homeostasis of the soluble, misfolded Aβ protein over the period of time. The method may include treating the subject determined to be responsive to the Aβ modulating therapy with the Aβ modulating therapy. The Aβ modulating therapy may include administration of one or more of: an inhibitor of BACE1 (beta-secretase 1); an inhibitor of γ-secretase; and a modulator of Aβ homeostasis, e.g., an immunotherapeutic modulator of Aβ homeostasis. The Aβ modulating therapy may include administration of one or more of: E2609; MK-8931; LY2886721; AZD3293; semagacestat (LY-450139); avagacestat (BMS-708163); solanezumab (SEQ ID NO: 11 (VH))(SEQ ID NO: 12 (VL)); crenezumab (SEQ ID NO: 13 (VH))(SEQ ID NO: 14 (VL)); bapineuzumab (SEQ ID NO: 15 (VH))(SEQ ID NO: 16 (VL)); BIIB037 (SEQ ID NO: 17 (VH))(SEQ ID NO: 18 (VL)); CAD106; 8F5 (SEQ ID NO: 19 (VH))(SEQ ID NO: 20 (VL)) or 5598 or other antibodies raised against Aβ globulomers, e.g., as described by Barghorn et al, "Globular amyloid β-peptide$_{1-42}$ oligomer—a homogenous and stable neuropathological protein in Alzheimer's disease" *J. Neurochem.*, 2005, 95, 834-847, the entire teachings of which are incorporated herein by reference; ACC-001; V950; Affitrope AD02; and the like.

In several embodiments, the method may include selectively concentrating the soluble, misfolded Aβ protein in one or more of the sample, the incubation mixture, and the detection mixture. The selectively concentrating the soluble, misfolded Aβ protein may include pre-treating the sample prior to forming the incubation mixture. The selectively concentrating the soluble, misfolded Aβ protein may include pre-treating the incubation mixture prior to incubating the incubation mixture. The selectively concentrating the soluble, misfolded Aβ protein may include contacting one or more Aβ specific antibodies to the soluble, misfolded Aβ protein to form a captured soluble, misfolded Aβ protein. The one or more Aβ specific antibodies may include one or more of: 6E10, 4G8, 82E1, A11, X-40/42, and 16ADV. Such antibodies may be obtained as follows: 6E10 and 4G8 (Covance, Princeton, N.J.); 82E1 (IBL America, Minneapolis, Minn.); A11 (Invitrogen, Carlsbad, Calif.); X-40/42 (MyBioSource, Inc., San Diego, Calif.); and 16ADV (Acumen Pharmaceuticals, Livermore, Calif.). The one or more Aβ specific antibodies may include one or more of: an antibody specific for an amino acid sequence of Aβ and an antibody specific for a conformation of the soluble, misfolded Aβ protein. The one or more Aβ specific antibodies may be coupled to a solid phase. The solid phase may include one or more of a magnetic bead and a multiwell plate.

For example, ELISA plates may be coated with the antibodies used to capture Aβ from the patient sample. The antibody-coated ELISA plates may be incubated with a patient sample, unbound materials may be washed off, and the PMCA reaction may be performed. Antibodies may also be coupled to beads. The beads may be incubated with the patient sample and used to separate Aβ-antibody complexes from the remainder of the patient sample.

In various embodiments, the contacting the sample with the monomeric Aβ protein to form the incubation mixture may include contacting a molar excess of the monomeric Aβ protein to the sample including the captured soluble, misfolded Aβ protein. The molar excess of the monomeric Aβ protein may be greater than a total molar amount of Aβ protein monomer included in the captured soluble, misfolded Aβ protein. The incubating the incubation mixture may be effective to cause oligomerization of at least a portion of the monomeric Aβ protein in the presence of the captured soluble, misfolded Aβ protein to form the amplified portion of the soluble, misfolded Aβ protein.

In some embodiments, the protein aggregate may include one or more of: the monomeric Aβ protein, the soluble, misfolded Aβ protein, a captured form of the soluble, misfolded Aβ protein, larger Aβ aggregates, and the like.

In several embodiments, the physically disrupting the incubation mixture may include one or more of: sonication, stirring, shaking, freezing/thawing, laser irradiation, autoclave incubation, high pressure, and homogenization. For example, shaking may include cyclic agitation. The cyclic agitation may be conducted between about 50 rotations per minute (RPM) and 10,000 RPM. The cyclic agitation may be conducted between about 200 RPM and about 2000 RPM. The cyclic agitation may be conducted at about 500 RPM.

In various embodiments, the physically disrupting the incubation mixture may be conducted in each incubation cycle for between about 5 seconds and about 10 minutes, between about 30 sec and about 1 minute, between about 45 sec and about 1 minute, for about 1 minute, and the like. For example, the physically disrupting the incubation mixture may be conducted in each incubation cycle by shaking for one or more of: between about 5 seconds and about 10 minutes, between about 30 sec and about 1 minute, between about 45 sec and about 1 minute, for about 1 minute, and the like. The incubating the incubation mixture may be independently conducted, in each incubation cycle, for a time between about 1 minutes and about 5 hours, between about 10 minutes and about 2 hours, between about 15 minutes and about 1 hour, between about 25 minutes and about 45 minutes, and the like. Each incubation cycle may include independently incubating and physically disrupting the incubation mixture for one or more of: incubating between about 1 minutes and about 5 hours and physically disrupting between about 5 seconds and about 10 minutes; incubating between about 10 minutes and about 2 hours and physically disrupting between about 30 sec and about 1 minute; incubating between about 15 minutes and about 1 hour and physically disrupting between about 45 sec and about 1 minute; incubating between about 25 minutes and about 45 minutes and physically disrupting between about 45 sec and about 1 minute; and incubating about 1 minute and physically disrupting about 1 minute.

The conducting the incubation cycle may be repeated between about 2 times and about 1000 times, between about 5 times and about 500 times, between about 50 times and about 500 times, between about 150 times and about 250 times, and the like. The incubating the incubation mixture being independently conducted, in each incubation cycle, at a temperature in ° C. of about 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, or a range between any two of the preceding values, for example, between about 15° C. and about 50° C.

In several embodiments, contacting the sample with the monomeric Aβ protein to form the incubation mixture may be conducted under physiological conditions. Contacting the sample with the monomeric Aβ protein to form the incubation mixture may include contacting the sample with a molar excess of the monomeric Aβ protein. The molar excess may be greater than a total molar amount of Aβ protein monomer included in the soluble, misfolded Aβ protein in the sample. The monomeric Aβ protein and/or the soluble, misfolded Aβ protein may include one or more peptides formed via β- or γ-secretase cleavage of amyloid precursor protein (SEQ ID NO: 1). The monomeric Aβ protein and/or the soluble, misfolded Aβ protein may include one or more of: Abeta40 (SEQ ID NO: 2) and Abeta42 (SEQ ID NO: 3).

In various embodiments of the methods described herein, the soluble, misfolded Aβ protein may substantially be the soluble, misfolded Aβ aggregate. The amplified portion of misfolded Aβ protein may substantially be one or more of: the amplified portion of the soluble, misfolded Aβ aggregate and the insoluble, misfolded Aβ aggregate. The monomeric, folded Aβ protein may be produced by one of: chemical synthesis, recombinant production, or extraction from non-recombinant biological samples.

In various embodiments, kits for determining a presence of a soluble, misfolded Aβ protein in a sample are provided. The kits may include one or more of a known amount of a monomeric Aβ protein and a known amount of an indicator of the soluble, misfolded Aβ protein. The kits may include instructions. The instructions may direct a user to contact the sample with one or more of the known amount of the monomeric, folded Aβ protein and the known amount of the indicator of the soluble, misfolded Aβ protein to form an incubation mixture. The instructions may direct a user to conduct an incubation cycle two or more times effective to form an amplified portion of misfolded Aβ protein from the monomeric, folded Aβ protein. Each incubation cycle may include incubating the incubation mixture effective to cause misfolding and/or aggregation of at least a portion of the monomeric, folded Aβ protein in the presence of the soluble, misfolded Aβ protein. Each incubation cycle may include physically disrupting the incubation mixture effective to at least partly de-aggregate at least a portion of a misfolded Aβ aggregate present. The instructions may direct a user to determine the presence of the soluble, misfolded Aβ protein in the sample by detecting at least a portion of the amplified portion of misfolded Aβ protein. The soluble, misfolded Aβ protein may include one or more of: a soluble, misfolded Aβ monomer and a soluble, misfolded Aβ aggregate. The amplified portion of misfolded Aβ protein may include one or more of: an amplified portion of the soluble, misfolded Aβ monomer, an amplified portion of the soluble, misfolded Aβ aggregate, and an insoluble, misfolded Aβ aggregate.

In various embodiments, the kits may include the known amount of the monomeric Aβ protein and the known amount of the indicator of the soluble, misfolded Aβ protein. The kits may include one or more of: a multiwall microtitre plate; a microfluidic plate; a shaking apparatus; an incubating apparatus; and a fluorescence measurement apparatus; included either as one or more of the individual plates and apparatuses, as a combination device, and the like. For example, a shaking microplate reader may be used to perform cycles of incubation and shaking and automatically measure the ThT fluorescence emission during the course of an experiment (e.g., FLUOstar OPTIMA, BMG LABTECH Inc., Cary, N.C.).

In several embodiments of the kits, an indicating state and a non-indicating state of the indicator of misfolded Aβ protein may be characterized by a difference in fluorescence, light absorption or radioactivity depending on the specific indicator. The instructions may direct the user to determine the presence of the soluble, misfolded Aβ protein in the sample by fluorescence, light absorption or radioactivity, or other forms of spectroscopy, depending on the specific indicator.

In some embodiments of the kits, the indicator of misfolded Aβ protein may include one or more of: Thioflavin T, Congo Red, m-I-Stilbene, Chrysamine G, PIB, BF-227, X-34, TZDM, FDDNP, MeO-X-04, IMPY, NIAD-4, luminescent conjugated polythiophenes, a fusion with a fluorescent protein such as green fluorescent protein and yellow fluorescent protein, derivatives thereof, and the like. The monomeric, folded Aβ protein may include one or more of a covalently incorporated radioactive amino acid, a covalently incorporated, isotopically labeled amino acid, and a covalently incorporated fluorophore.

In various embodiments of the kits, the instructions may direct a user to conduct any of the methods described herein. For example, the instructions may include directions to the user to determine an amount of the soluble, misfolded Aβ protein in the sample. The instructions may direct the user to detect the soluble, misfolded Aβ protein in the detection mixture by conducting one or more of: a Western Blot assay, a dot blot assay, an enzyme-linked immunosorbent assay (ELISA), a thioflavin T binding assay, a Congo Red binding assay, a sedimentation assay, electron microscopy, atomic force microscopy, surface plasmon resonance, spectroscopy, and the like.

The instructions may direct the user to detect the soluble, misfolded Aβ protein in the detection mixture by contacting the detection mixture with a protease; and detecting the soluble, misfolded Aβ protein in the detection mixture using anti-misfolded protein antibodies in one or more of: a Western Blot assay, a dot blot assay, and an ELISA.

In several embodiments of the kits, the instructions may direct the user to take the sample from a subject. The instructions may include directing the user to determine the presence of AD in the subject according to the presence of the soluble, misfolded Aβ protein in the sample. The presence of the soluble, misfolded Aβ protein in the sample may be determined compared to a control sample taken from a control subject. The instructions may direct the user to determine the presence of AD in the subject by comparing the amount of the soluble, misfolded Aβ protein in the sample to a predetermined threshold amount. The instructions may direct the user to obtain the sample including one or more of: amniotic fluid; bile; blood; cerebrospinal fluid; cerumen; skin; exudate; feces; gastric fluid; lymph; milk; mucus, e.g. nasal secretions; mucosal membrane, e.g., nasal mucosal membrane; peritoneal fluid; plasma; pleural fluid; pus; saliva; sebum; semen; sweat; synovial fluid; tears; and urine. The instructions may direct the user to determine a progression or homeostasis of AD in the subject by comparing the amount of the soluble, misfolded Aβ protein in the sample to an amount of the soluble, misfolded Aβ protein in a comparison sample taken from the subject at a different time compared to the sample.

The instructions may direct the user to the user to selectively concentrate the soluble, misfolded Aβ protein in one or more of the sample, the incubation mixture and the detection mixture. For example, the kit may include one or more Aβ specific antibodies configured to selectively concentrate or capture the soluble, misfolded Aβ protein. The one or more Aβ specific antibodies may include one or more of: an antibody specific for an amino acid sequence of Aβ or an antibody specific for a conformation of the soluble, misfolded Aβ protein. The one or more Aβ specific antibodies may include one or more of: 6E10, 4G8, 82E1, A11, X-40/42, and 16ADV. The instructions may direct the user to selectively concentrate the soluble, misfolded Aβ protein by contacting the one or more Aβ specific antibodies to the soluble, misfolded Aβ protein to form a captured soluble, misfolded Aβ protein. The one or more Aβ specific antibodies may be provided coupled to a solid phase. The solid phase may include one or more of a magnetic bead and a multiwell plate.

In various embodiments of the kit, the instructions for physically disrupting the incubation mixture may direct the user to employ one or more of: sonication, stirring, shaking, freezing/thawing, laser irradiation, autoclave incubation, high pressure, homogenization, and the like. The instructions may direct the user to conduct cyclic agitation according to any RPM range described herein, for example, between about 50 RPM and 10,000 RPM. The instructions may direct the user to conduct the physical disruption in each incubation cycle according to any time range described herein, for example, between about 5 seconds and about 10 minutes. The instructions may direct the user to incubate the incubation mixture in each incubation cycle according to any time range described herein, for example, for a time between about 1 minutes and about 5 hours. The instructions for conducting the incubation cycle may direct the user to conduct the incubation cycle for any number of repetitions described herein, for example, between about 2 times and about 1000 times. Instructions for conducting the incubation cycle may include directions to a user to incubate at a temperature between about 15° C. and about 50° C.

In various embodiments of the kits described herein, the soluble, misfolded Aβ protein may substantially be the soluble, misfolded Aβ aggregate. The amplified portion of misfolded Aβ protein may substantially be one or more of: the amplified portion of the soluble, misfolded Aβ aggregate and the insoluble, misfolded Aβ aggregate. The monomeric, folded Aβ protein may be produced by one of: chemical synthesis, recombinant production, or extraction from non-recombinant biological samples.

EXAMPLES

Example 1: Preparation of Synthetic Aβ Oligomers

Aβ1-42 (SEQ ID NO: 3) was synthesized using solid-phase N-tert-butyloxycarbonyl chemistry at the W. Keck Facility at Yale University and purified by reverse-phase HPLC. The final product was lyophilized and characterized by amino acid analysis and mass spectrometry. To prepare stock solutions free of aggregated, misfolded Aβ protein, aggregates were dissolved high pH and filtration through 30 kDa cut-off filters to remove remaining aggregates. To prepare different types of aggregates, solutions of seed-free Aβ1-42 (SEQ ID NO: 3) (10 µM) were incubated for different times at 25° C. in 0.1 M Tris-HCl, pH 7.4 with agitation. This preparation contained a mixture of Aβ monomers as well as fibrils, protofibrils and soluble, misfolded Aβ protein in distinct proportions depending on the incubation time. The degree of aggregation was characterized by ThT fluorescence emission, electron microscopy after negative staining, dot blot studies with the A11 conformational antibody and western blot after gel electrophoresis using the 4G8 anti-Aβ antibody.

A mixture of Aβ oligomers of different sizes were generated during the process of fibril formation. Specifically, soluble, misfolded Aβ protein was prepared by incubation of monomeric synthetic Aβ1-42 (SEQ ID NO: 3) (10 µM) at 25° C. with stirring. After 5 h of incubation, an abundance of soluble, misfolded Aβ protein, globular in appearance, was observed by electron microscopy after negative staining, with only a small amount of protofibrils and fibrils observed. At 10 h there are mostly protofibrils and at 24 h, a large amount of long fibrils are observed. FIG. 1A shows electron micrographs taken at 0 h, 5 h, 10 h, and 24 h of incubation.

Figure 1B:
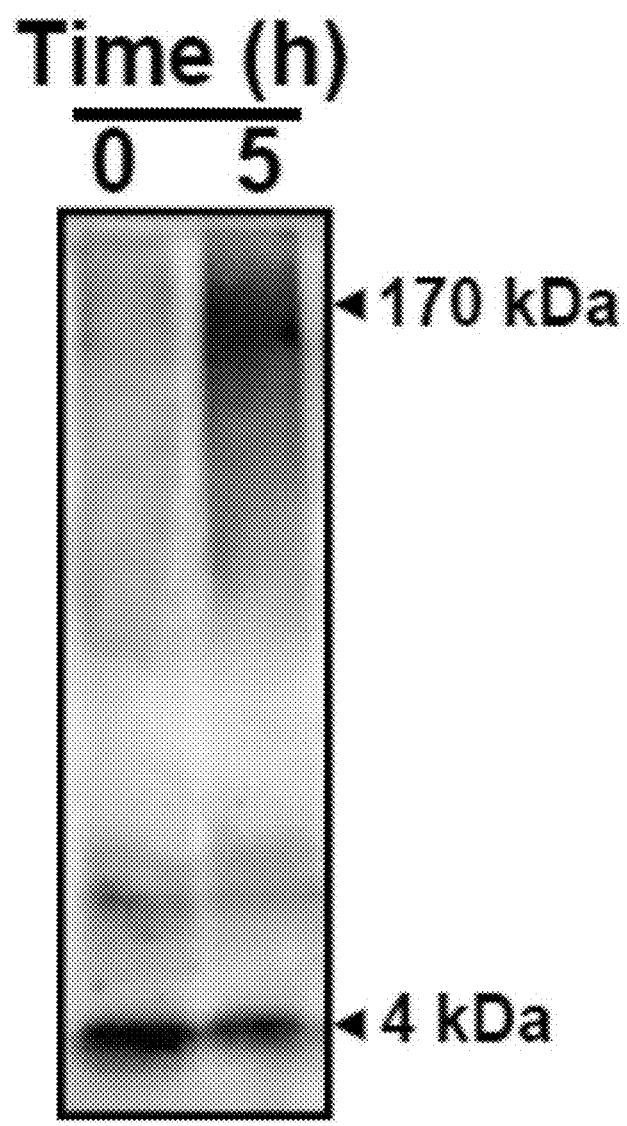
FIG. 1B is a western blot of soluble oligomeric Aβ protein aggregates.

The soluble, misfolded Aβ protein aggregates tested positive using A11 anti-oligomer specific antibody according to the method of Kayed, et al. "Common structure of soluble amyloid oligomers implies common mechanism of pathogenesis," Science 2003, 300, 486-489. After further incubation at 10 h and 24 h, protofibrillar and fibrillar structures were observed. The size of the aggregates was determined by filtration through filters of defined pore size and western blotting after SDS-PAGE separation. Soluble, misfolded Aβ protein formed by incubation for 5 h was retained in filters of 30 kDa cut-off and passed through 1000 kDa cutoff filters. FIG. 1B is a western blot of soluble, misfolded Aβ protein aggregates. Electrophoretic separation of this soluble, misfolded Aβ protein showed that the majority of the material migrated as ~170 kDa SDS-resistant aggregates, with a minor band at 17 kDa.

Example 2: Aβ-PMCA Detects Synthetic Aβ Oligomers

Example 2A

Figure 2A:
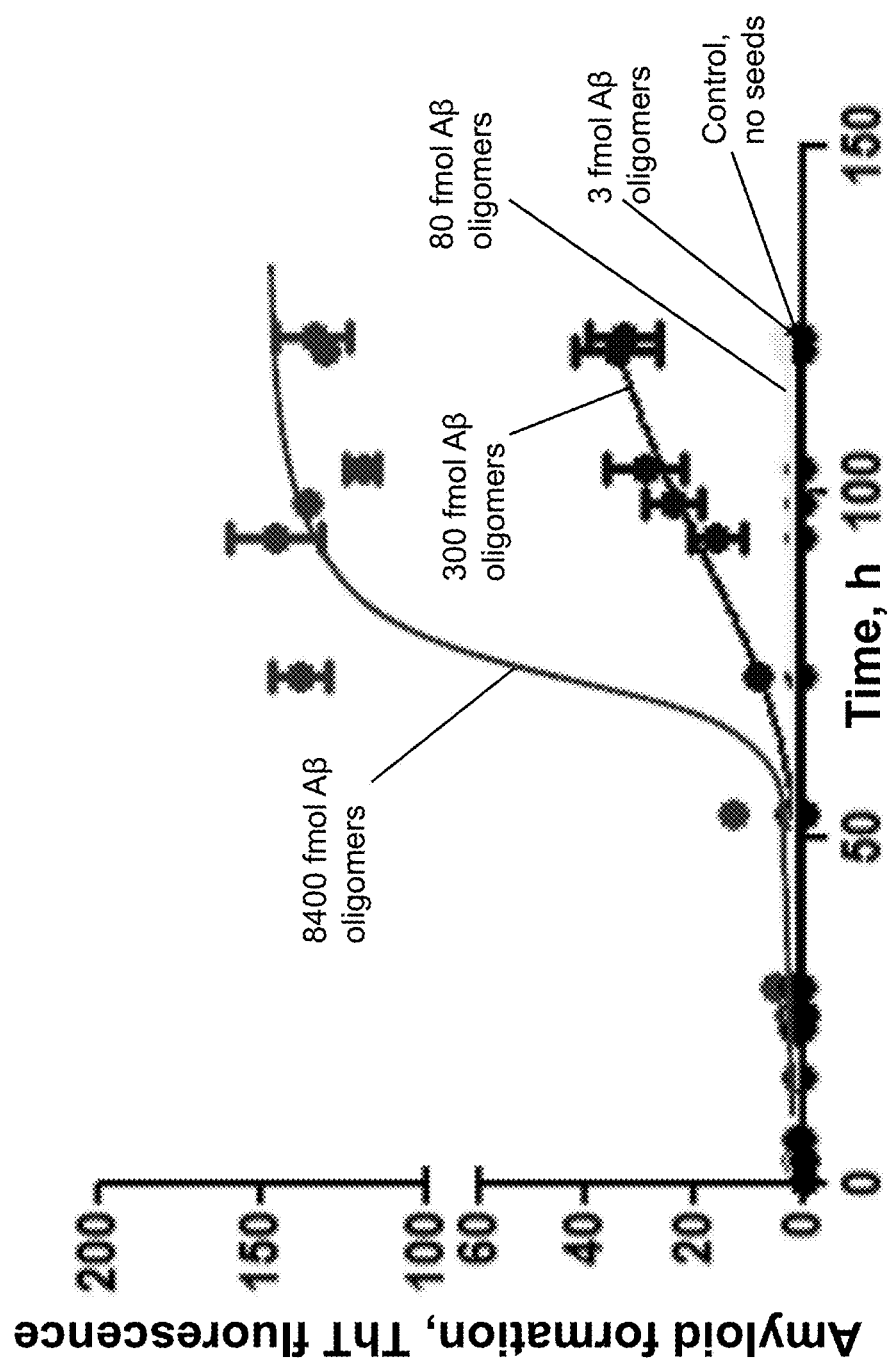
FIG. 2A is a graph showing non-amplified amyloid formation measured by ThT fluorescence as a function of time seeded by various concentrations of synthetic soluble oligomeric Aβ protein of EXAMPLE 1.

Seeding of Aβ aggregation was studied by incubating a solution of seed-free Aβ1-42 (SEQ ID NO: 3) in the presence of Thioflavin T with or without different quantities of synthetic soluble, misfolded Aβ protein (Control (no Aβ oligomer); or 3, 80, 300, and 8400 femtomolar in synthetic soluble, misfolded Aβ protein). Aβ-PMCA general procedure: Solutions of 2 µM aggregate-free Aβ1-42 (SEQ ID NO: 3) in 0.1 M Tris-HCl pH 7.4 (200 µL total volume) were placed in opaque 96-wells plates and incubated alone or in the presence of synthetic Aβ aggregates (prepared by incubation over 5 h as described in EXAMPLE 1) or 40 μL of CSF aliquots. Samples were incubated in the presence of 5 μM Thioflavin T (ThT) and subjected to cyclic agitation (1 min at 500 rpm followed by 29 min without shaking) using an Eppendorf thermomixer, at a constant temperature of 22° C. At various time points, ThT fluorescence was measured in the plates at 485 nm after excitation at 435 nm using a plate spectrofluorometer. FIG. 2A is a graph of amyloid formation (without cyclic amplification) versus time as measured by Thioflavin T fluorescence, using the indicated femtomolar concentration of synthetic soluble, misfolded Aβ protein seeds. The peptide concentration, temperature and pH of the buffer were monitored to control the extent of the lag phase and reproducibility among experiments. Under these conditions, no spontaneous Aβ aggregation was detected during the time in which the experiment was performed (125 h). Aggregation of monomeric Aβ1-42 protein (SEQ ID NO: 3) was observed in the presence of 0.3 to 8.4 fmol of the synthetic soluble, misfolded Aβ protein of EXAMPLE 1.

Example 2B

Figure 2B:
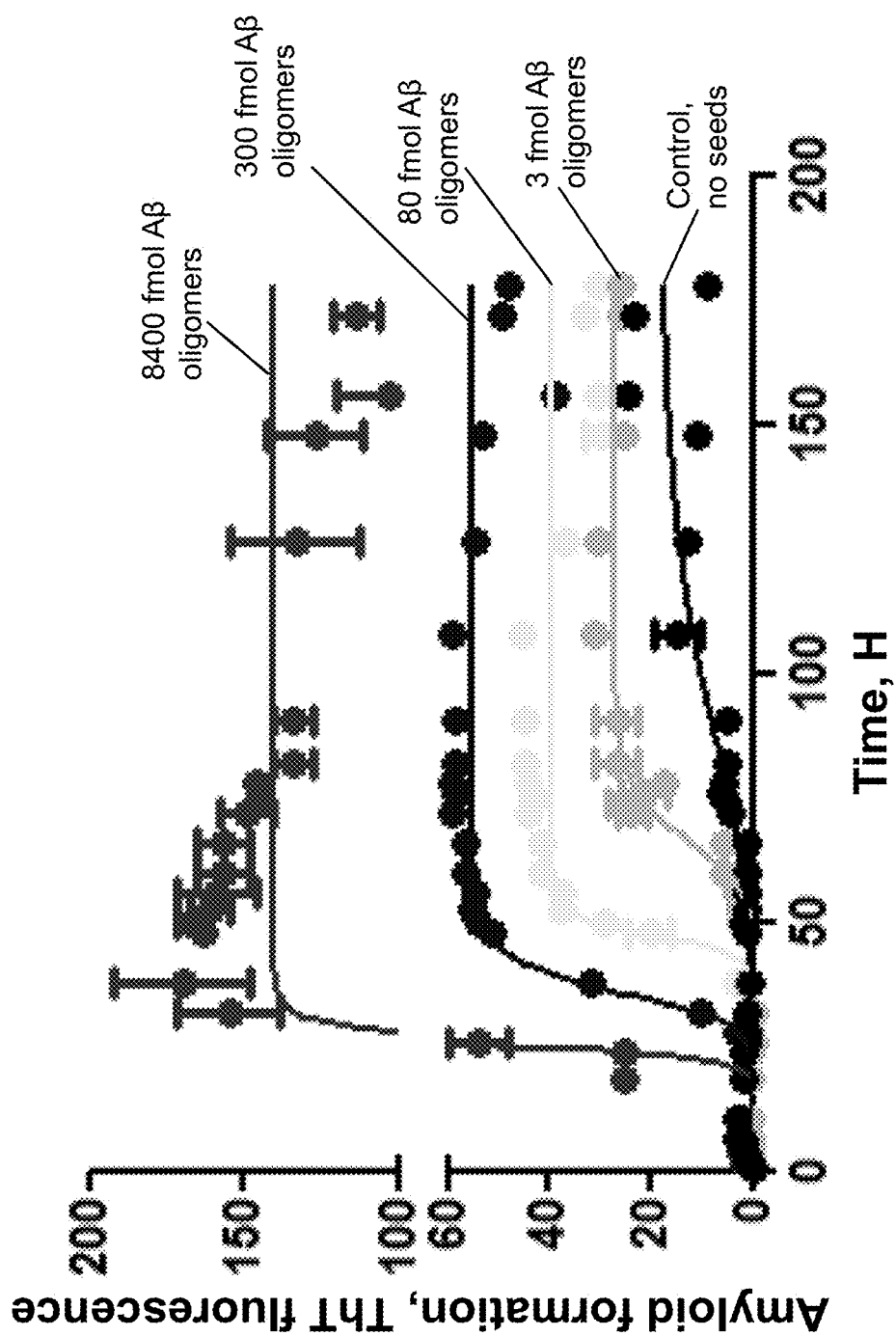
FIG. 2B is a graph showing amplification cycle-accelerated amyloid formation measured by ThT fluorescence as a function of time seeded by various concentrations of synthetic soluble oligomeric Aβ protein of EXAMPLE 1.

Amplification cycles, combining phases of incubation and physical disruption were employed. The same samples as in FIG. 2A were incubated with cyclic agitation (1 min stirring at 500 rpm followed by 29 min without shaking). Aggregation was measured over time by the thioflavin T (ThT) binding to amyloid fibrils using a plate spectrofluorometer (excitation: 435; emission: 485 nm). Graphs show the mean and standard error of 3 replicates. The concentration of Aβ oligomers was estimated assuming an average molecular weight of 170 kDa. FIG. 2B is a graph showing amplification cycle-accelerated amyloid formation measured by ThT fluorescence as a function of time for various concentrations of the synthetic soluble, misfolded Aβ protein of EXAMPLE 1. Under these conditions, the aggregation of monomeric Aβ1-42 protein (SEQ ID NO: 3) induced by 8400, 300, 80 and 3 fmol of the synthetic soluble, misfolded Aβ protein was clearly faster and more easily distinguished from that observed in the absence of the synthetic soluble, misfolded Aβ protein. This result indicates the detection limit, under these conditions, is 3 fmol of soluble, misfolded Aβ protein or less in a given sample.

Example 3: Aβ-PMCA Detects Misfolded Aβ in the Cerebrospinal Fluid of AD Patients Aliquots of CSF were obtained from 50 AD patients, 39 cognitively normal individuals affected by non-degenerative neurological diseases (NND), and 37 patients affected by non-AD neurodegenerative diseases including other forms of dementia (NAND). Test CSF samples were obtained from 50 patients with the diagnosis of probable AD as defined by the DSM-IV and the NINCDS-ADRA guidelines (McKhann et al., 1984) and determined using a variety of tests, including routine medical examination, neurological evaluation, neuropsychological assessment, magnetic resonance imaging and measurements of CSF levels of Aβ1-42 (SEQ ID NO: 3), total Tau and phospho-Tau. The mean age of AD patients at the time of sample collection was 71.0±8.1 years (range 49-84). Control CSF samples were obtained from 39 patients affected by non-degenerative neurological diseases (NND), including 12 cases of normal pressure hydrocephalus, 7 patients with peripheral neuropathy, 7 with diverse forms of brain tumor, 2 with ICTUS, 1 with severe cephalgia, 3 with encephalitis, 1 with hypertension and 6 with unclear diagnosis. The mean age at which CSF samples were taken from this group of patients was 64.6±14.7 years (range 31-83). Control CSF samples were also taken from 37 individuals affected by non-AD neurodegenerative diseases (NAND), including 10 cases of fronto-temporal dementia (5 behavioral and 5 language variants), 6 patients with Parkinson's disease (including 4 associated with dementia and 1 with motor neuron disease), 6 with progressive supranuclear palsy, 6 with spinocerebellar ataxia (1 associated with dementia), 4 with amyotrophic lateral sclerosis, 2 with Huntington's disease, 1 with MELAS, 1 with Lewy body dementia, and 1 with vascular dementia. The mean age at sample collection for this group was 63.8±11.1 years (range 41-80). CSF samples were collected in polypropylene tubes following lumbar puncture at the L4/L5 or L3/L4 interspace with atraumatic needles after one night fasting. The samples were centrifuged at 3,000 g for 3 min at 4° C., aliquoted and stored at −80° C. until analysis. CSF cell counts, glucose and protein concentration were determined. Albumin was measured by rate nephelometry. To evaluate the integrity of the blood brain barrier and the intrathecal IgG production, the albumin quotient (CSF albumin/serum albumin)×$10^3$ and the IgG index (CSF albumin/serum albumin)/(CSF IgG/serum IgG) were calculated. The study was conducted according to the provisions of the Helsinki Declaration and was approved by the Ethics Committee.

Figure 3A:
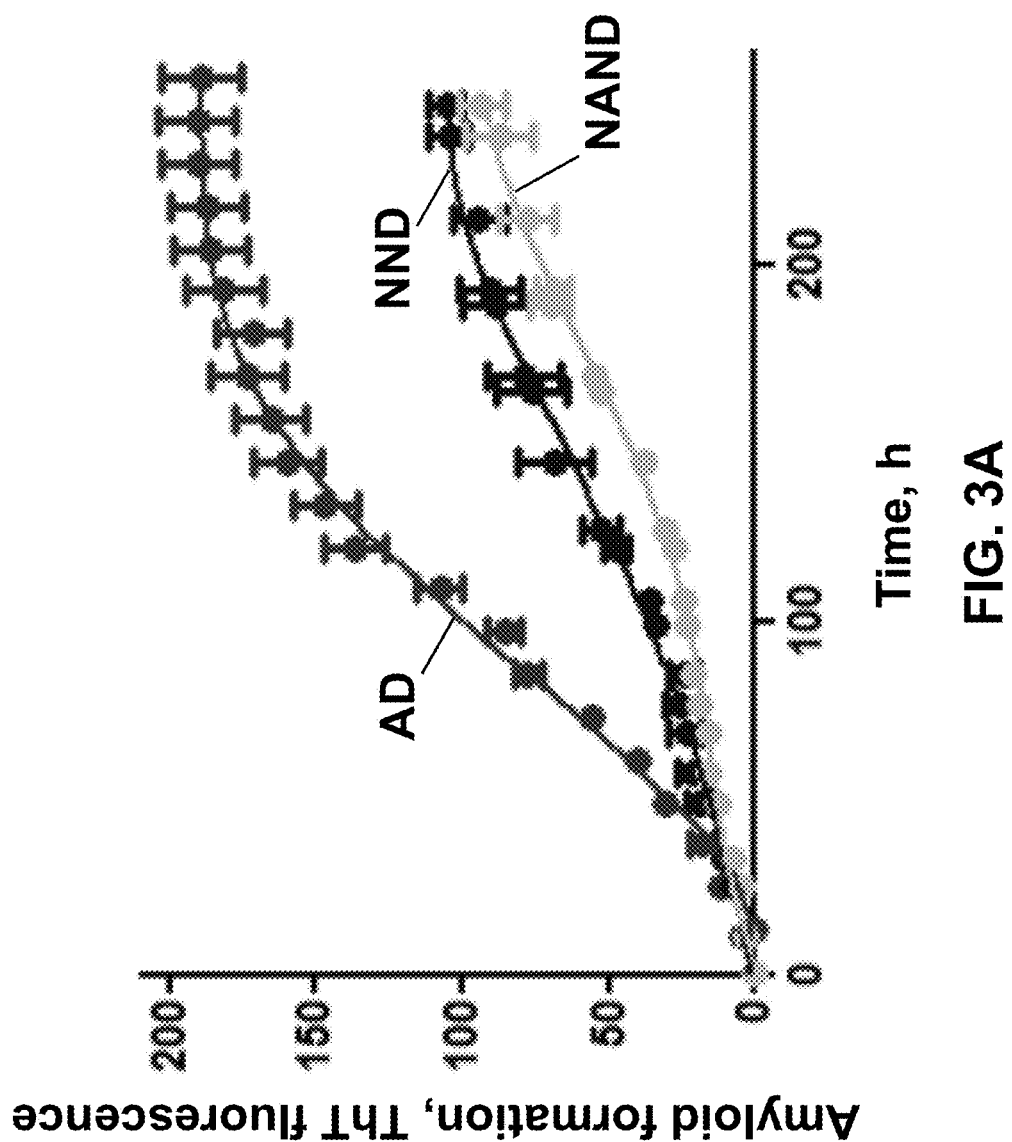
FIG. 3A is a graph of amyloid formation versus time, measured as a function of ThT fluorescence labeling, showing the average kinetics of Aβ aggregation seeded by CSF from 5 representative samples from the AD, NND, and NAND groups.

The experiments as well as the initial part of the analysis were conducted blind. FIG. 3A is a graph of amyloid formation versus time, measured as a function of ThT fluorescence labeling, showing the average kinetics of Aβ aggregation of 5 representative samples from the AD, NND, and NAND groups.

The results indicate that CSF from AD patients significantly accelerates Aβ aggregation as compared to control CSF ($P<0.001$). The significance of the differences in Aβ aggregation kinetics in the presence of human CSF samples was analyzed by one-way ANOVA, followed by the Tukey's multiple comparison post-test. The level of significance was set at $P<0.05$. The differences between AD and samples from the other two groups were highly significant with $P<0.001$ (***).

Figure 3B:
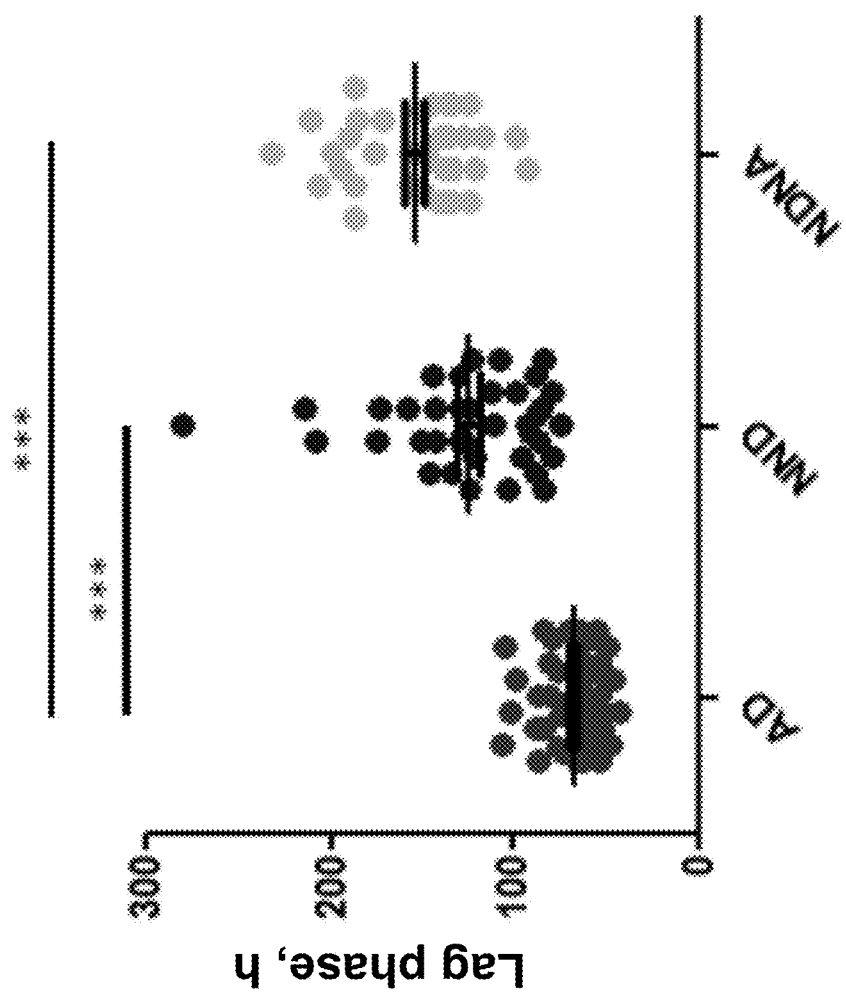
FIG. 3B is a graph of the lag phase time in h for Aβ aggregation in the presence of samples from the AD, NND, and NAND groups.

FIG. 3B is a graph of the lag phase time in h for samples from the AD, NND, and NAND groups. To determine the effect of individual samples on Aβ aggregation, the lag phase was estimated, defined as the time to ThT fluorescence larger than 40 arbitrary units after subtraction of a control buffer sample. This value was selected considering that it corresponds to ~5 times the reading of the control buffer sample.

Figure 3C:
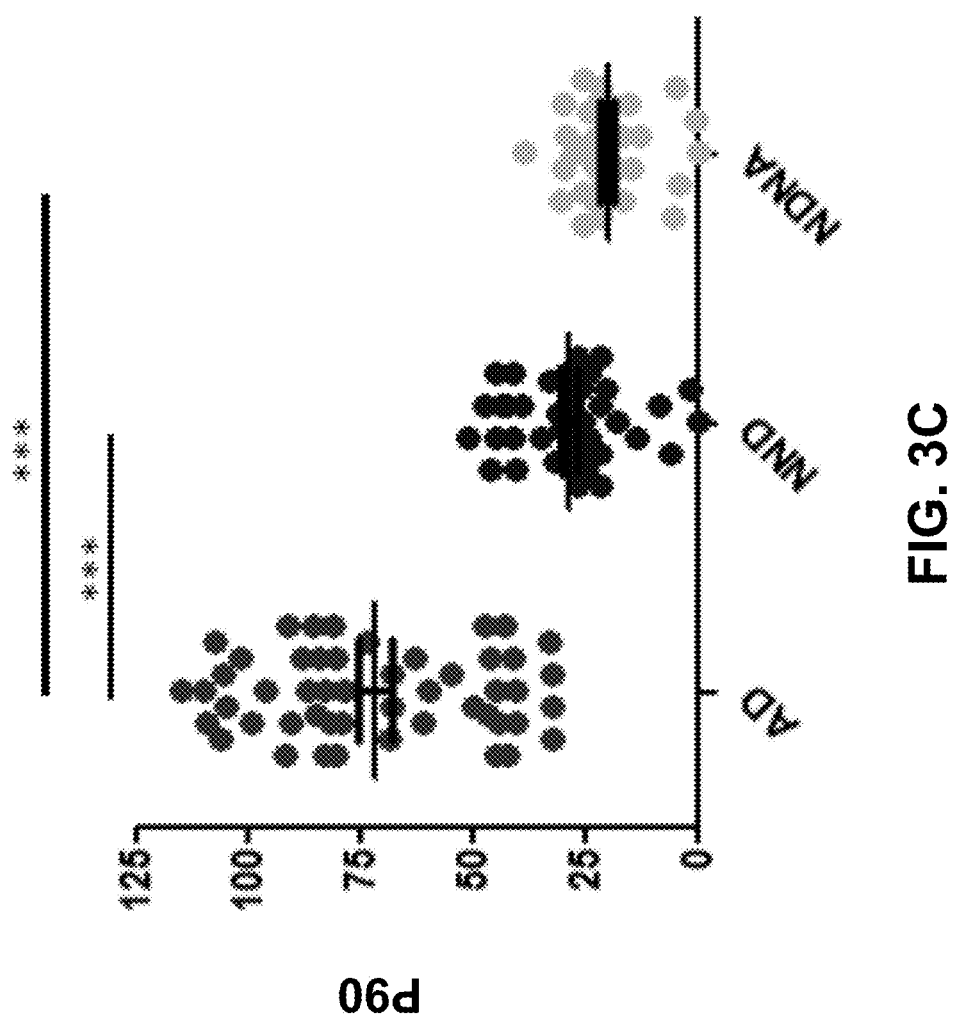
FIG. 3C is a graph showing the extent of amyloid formation obtained after 180 Aβ-PMCA cycles, i.e. 90 h of incubation (P90) in the presence of CSF samples from AD, NND and NAND patients.

FIG. 3C is a graph showing the extent of amyloid formation obtained after 180 Aβ-PMCA cycles, i.e. 90 h of incubation (P90). Comparison of the lag phase and P90 among the experimental groups reveals a significant difference between AD and control samples from individuals with non-degenerative neurological diseases or with non-AD neurodegenerative diseases. Further, no correlation was detected between the aggregation parameters and the age of the AD patients, which indicates that the levels of the marker corresponds to aggregated Aβ protein in patient CSF, and not patient age.

FIG. 5, Table 1 shows estimations of the sensitivity, specificity and predictive value of the Aβ-PMCA test, calculated using the lag phase numbers.

Figure 6:
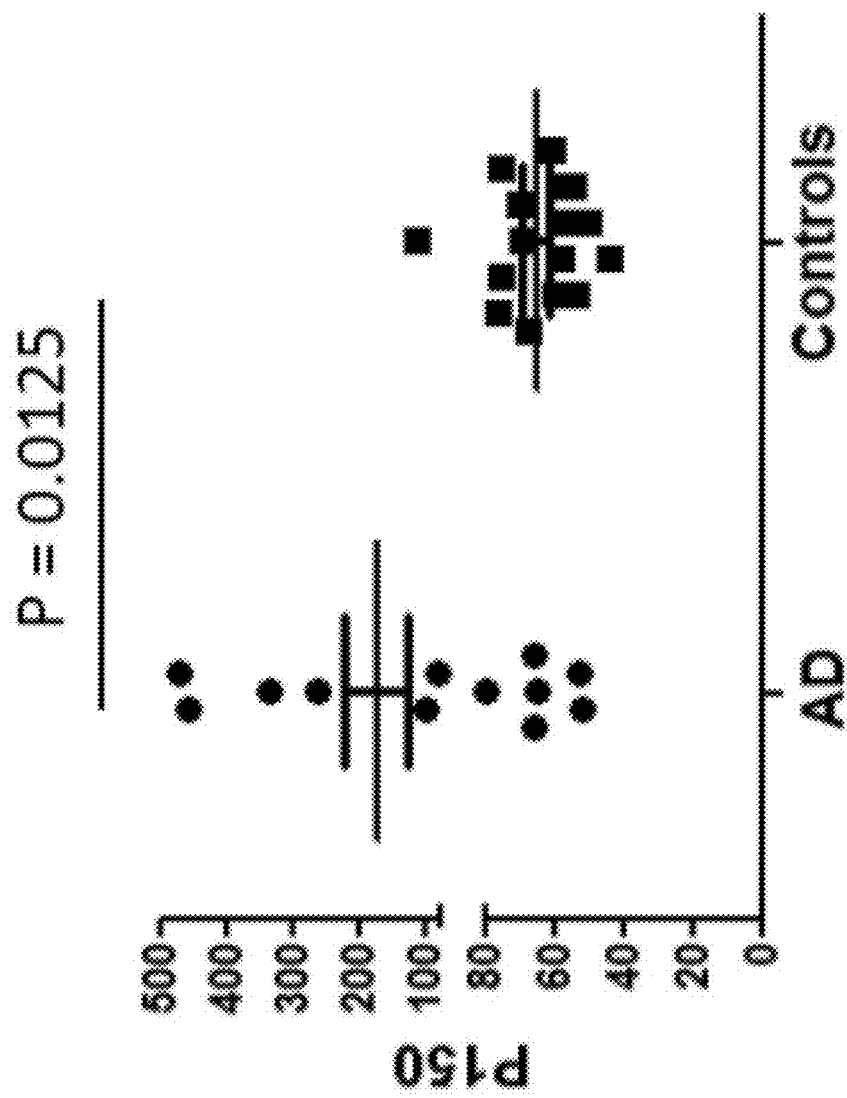
FIG. 6 is a graph of the lag phase time in h for samples obtained after 300 Aβ-PMCA cycles, i.e. 150 h of incubation (P90) in the presence of CSF samples from AD and control patients.

To study reproducibility, an experiment similar to the one shown in FIGS. 3A-C was independently done with different samples, reagents and a new batch of Aβ peptide as substrate for Aβ-PMCA. The extent of amyloid formation obtained after 300 Aβ-PMCA cycles, i.e. 150 h of incubation (P150), was measured in each patient. The control group includes both people affected by other neurodegenerative diseases and non-neurologically sick patients. Data for each sample represent the average of duplicate tubes. Statistical differences were analyzed by student-t test. FIG. 6 is a graph of the lag phase time in h for samples obtained after 300 Aβ-PMCA cycles, i.e. 150 h of incubation (P90).

During the course of the study an entire set of CSF samples coming from a fourth location did not aggregate at all, even after spiking with large concentrations of synthetic oligomers. It is expected that reagent contamination during sample collection interfered with the assay.

The differences in aggregation kinetics between different samples were evaluated by the estimation of various different kinetic parameters, including the lag phase, A50, and P90. Lag phase is defined as the time required to reach a ThT fluorescence higher than 5 times the background value of the buffer alone. The A50 corresponds to the time to reach 50% of maximum aggregation. P90 corresponds to the extent of aggregation (measured as ThT fluorescence) at 90 h. Sensitivity, specificity and predictive value were determined using this data, with cutoff thresholds determined by Receiver Operating Characteristics (ROC) curve analysis, using MedCalc software (MedCalc Software, Ostend, Belgium).

Example 4: Determination of Threshold Values of Misfolded aβ for Aβ-PMCA Detection of AD in CSF In support of FIG. 5, TABLE 1, sensitivity, specificity and predictive value were determined using the lag phase data, with cutoff thresholds determined by Receiver Operating Characteristics (ROC) curve analysis, using the MedCalc software (version 12.2.1.0, MedCalc, Belgium). As shown in FIG. 5, TABLE 1, a 90.0% sensitivity and 84.2% specificity was estimated for the control group consisting of age-matched individuals with non-degenerative neurological diseases. By contrast, for the clinically more relevant differentiation of AD from other neurodegenerative diseases including other forms of dementia, 100% sensitivity and 94.6% specificity was estimated. This ability of Aβ-PMCA to distinguish AD from other forms of neurodegenerative diseases is clinically significant. The overall sensitivity and specificity considering all control individuals was 90% and 92%, respectively.

Figure 4A:
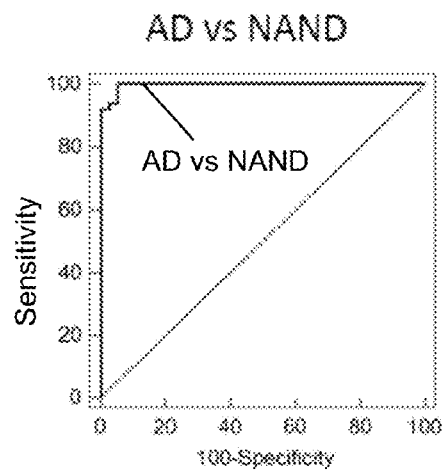
FIG. 4A is a plot of the true positive rate (sensitivity) as a function of the false positive rate (specificity) for different cut-off points using the lag phase values showed in FIG. 3B for AD vs. NAND.
Figure 4B:
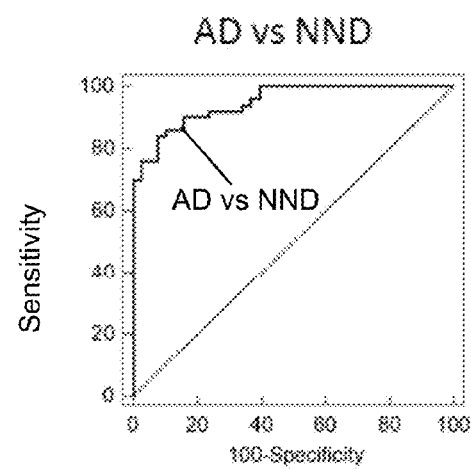
FIG. 4B is a plot of the true positive rate (sensitivity) as a function of the false positive rate (specificity) for different cut-off points using the lag phase values showed in FIG. 3B for AD vs NND.
Figure 4C:
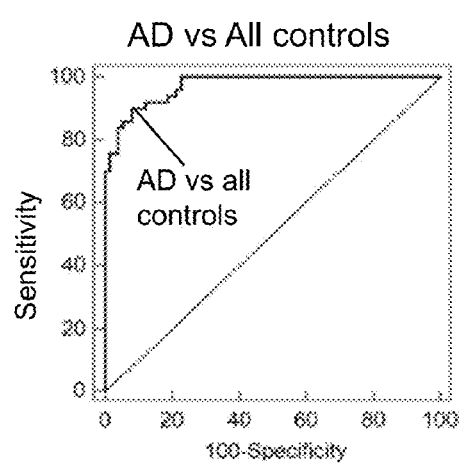
FIG. 4C is a plot of the true positive rate (sensitivity) as a function of the false positive rate (specificity) for different cut-off points using the lag phase values showed in FIG. 3B for AD vs A11 control samples.
Figure 4D:
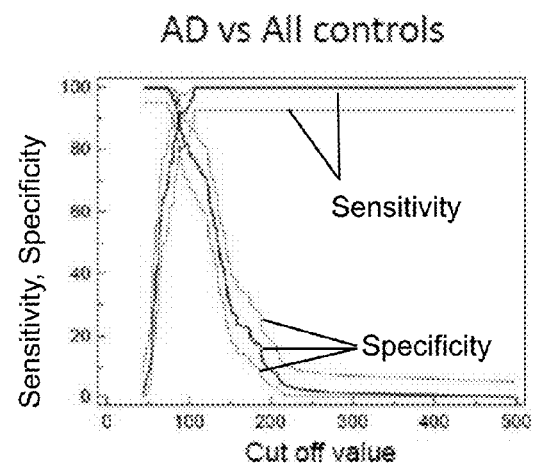
FIG. 4D is a plot of the true positive rate (sensitivity) as a function of the false positive rate (specificity) for different cut-off points using the lag phase values showed in FIG. 3B and estimates the most reliable cut-off point for the different set of group comparisons of FIGS. 4A-4C.

To evaluate the performance of the Aβ-PMCA test to distinguish AD patients from controls, the true positive rate (sensitivity) was plotted as a function of the false positive rate (specificity) for different cut-off points. For this analysis the lag phase values for AD vs NAND (FIG. 4A), AD vs NND (FIG. 4B) and AD vs A11 control samples (FIG. 4C) was used. The performance of the test, estimated as the area under the curve was 0.996±0.0033, 0.95±0.020 and 0.97±0.011 for the comparison of AD with NAND, NND and all controls, respectively. Statistical analysis was done using the MedCalc ROC curve analysis software (version 12.2.1.0) and the result indicated that the test can distinguish AD from the controls with a $P<0.0001$. To estimate the most reliable cut-off point for the different set of group comparisons, sensitivity (blue line) and specificity (red line) were plotted for each cut-off value (FIG. 4D). The graph shows the curve and the 95% confidence intervals for the AD vs all control samples (including NAND and NND groups). These cut-off values were used to estimate sensitivity, specificity and predictive value in FIG. 5, Table 1.

Figure 7A:
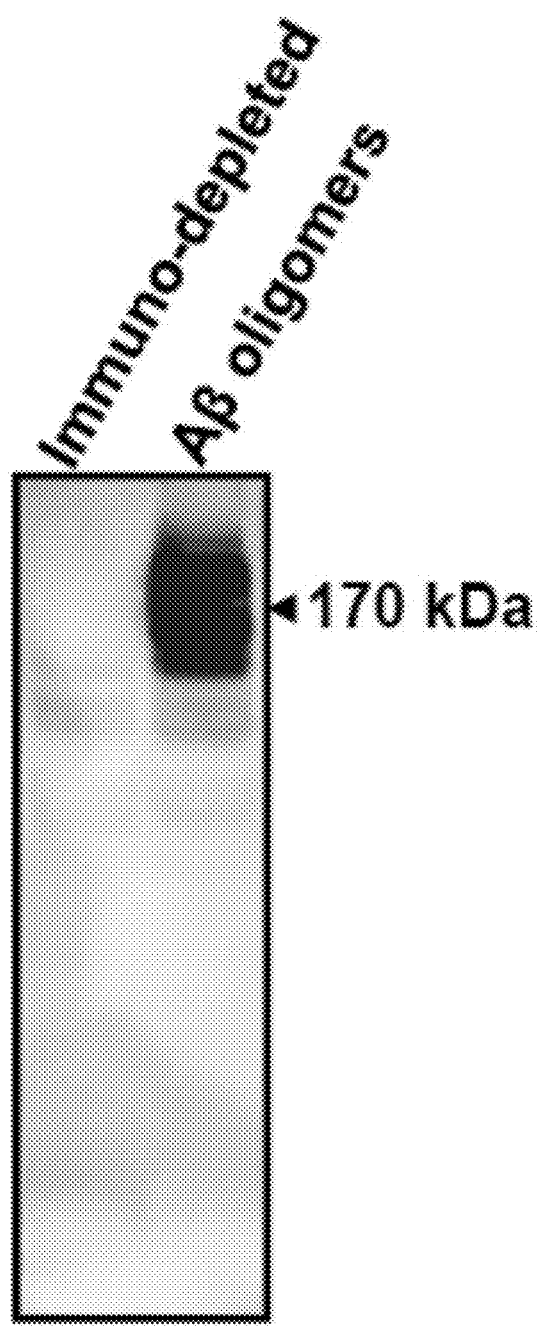
FIG. 7A is a western blot showing results of immunodepletion using synthetically prepared Aβ oligomers spiked into human CSF.

Example 5: Aβ-Oligomer Immunodepletion Removes Aβ Seeds in Human Cerebrospinal Fluid and Confirms Aβ-PMCA Detects Soluble Misfolded Aβ Protein in AD CSF Immunodepletion experiments were performed to confirm that Aβ-PMCA detects a seeding activity associated to soluble, misfolded Aβ protein present in CSF. The methodology for efficient immunodepletion of soluble, misfolded Aβ protein was first optimized by using synthetically prepared soluble, misfolded Aβ protein. Immunodepletion was performed by incubation with dynabeads conjugated with a mixture of antibodies recognizing specifically the sequence of Aβ (4G8) and conformational (A11) antibodies. FIG. 7A is a western blot showing results of immunodepletion using synthetically prepared Aβ oligomers spiked into human CSF. Soluble, misfolded Aβ protein was efficiently removed by this immunodepletion.

Figure 7B:
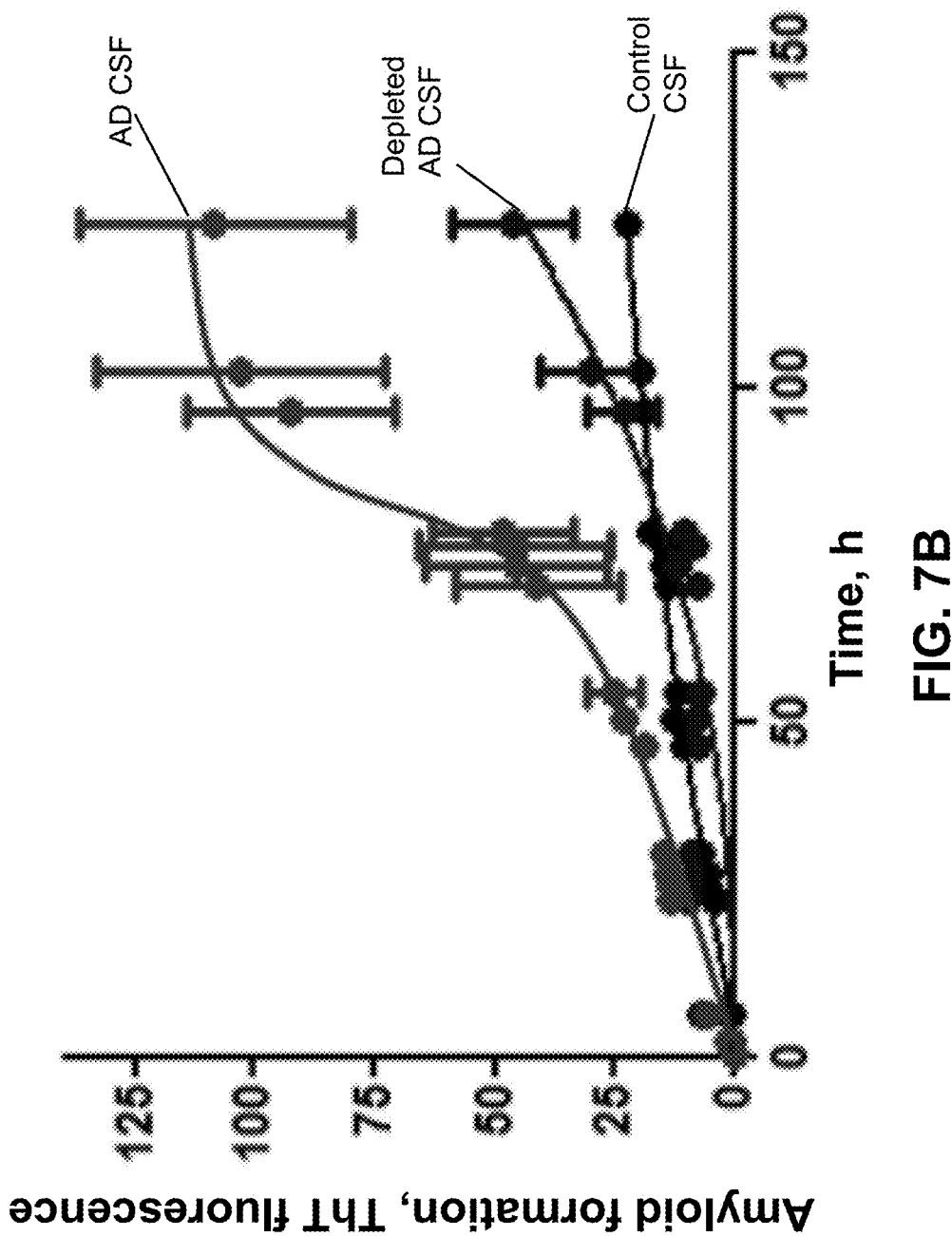
FIG. 7B is a graph showing the kinetics of Aβ aggregation seeded by control and immunodepleted CSF samples.
Figure 7C:
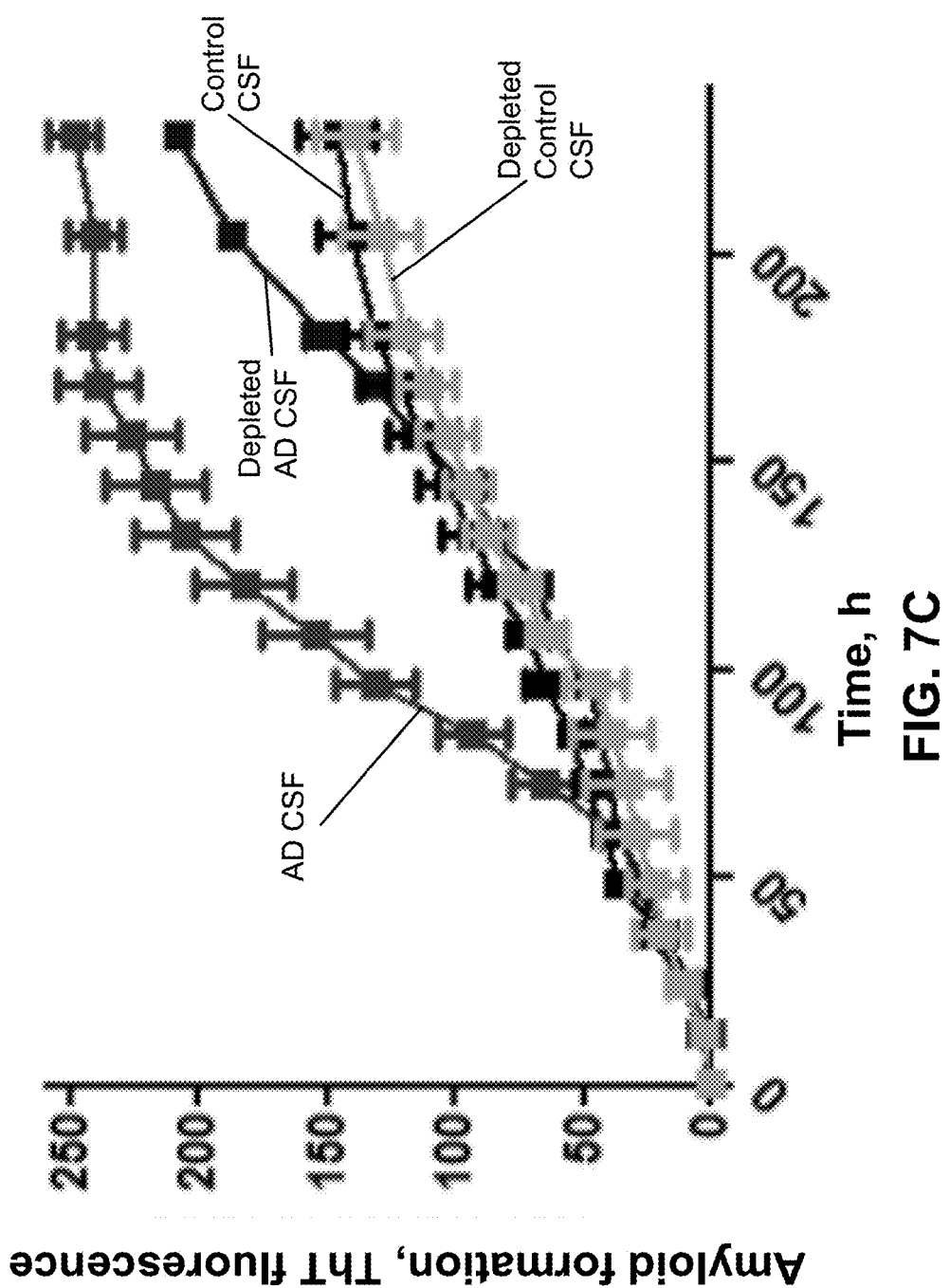
FIG. 7C is a graph showing the kinetics of Aβ aggregation seeded by control and immunodepleted CSF samples, depleted only with the A11 conformational antibody.

FIGS. 7A and 7B are graphs of amyloid formation versus time as measured by Thioflavin T fluorescence, demonstrating that seeding activity in AD CSF is removed by soluble, misfolded Aβ protein immuno-depletion. Samples of AD CSF before or after immunodepletion with 4G8 and A11 antibodies were used to seed Aβ aggregation in the Aβ-PMCA assay. Immunodepletion was applied to 3 AD CSF. FIG. 7B is a graph showing the kinetics of control and immunodepleted CSF samples. FIG. 7B shows that for immunodepleted AD CSF, the kinetics of Aβ aggregation in the Aβ-PMCA reaction was comparable to that observed in control CSF samples, and both were significantly different from the aggregation observed with AD CSF prior to immunodepletion. FIG. 7C is a graph showing the kinetics of control and immunodepleted CSF samples, depleted only with the A11 conformational antibody and aggregation monitored by Aβ-PMCA assay. FIG. 7C shows similar results, obtained using AD CSF immunodepleted using the A11 conformational antibody, which specifically recognizes, misfolded Aβ. These results confirm that Aβ-PMCA detects soluble, misfolded β protein in AD CSF.

Example 6: Solid Phase Immuno Capturing

FIGS. 8A and 8B are schematic representations of two solid phase methods used to capture soluble, misfolded Aβ protein from complex samples such as blood plasma. Strategy 1 employed ELISA plates pre-coated with specific antibodies bound to a solid phase on the ELISA plate. After washing the plates, the Aβ-PMCA reaction was carried out in the same plates. Strategy 2 used magnetic beads as the solid phase coated with specific antibodies. This approach provided concentration of the samples.

Example 7: Specificity of Immuno Capturing

FIG. 9 shows Table 2, demonstrating the ability of specific antibodies to capture the Aβ oligomers. The top panel shows a schematic representation of the epitope recognition site on the Aβ protein of the diverse sequence antibodies used in this study. Table 2 in FIG. 9 demonstrates the efficiency of different sequence or conformational antibodies to capture Aβ oligomers. The capacity to capture oligomers was measured by spiking synthetic Aβ oligomers in healthy human blood plasma and detection by Aβ-PMCA. The symbols indicate that the detection limits using the different antibodies were: <12 fmol (+++); between 10-100 fmol (++); >1 pmol (+) and not significantly higher than without capturing reagent (−).

Example 8: Detection of aβ Oligomers Spiked in Human Plasma

Figure 10:
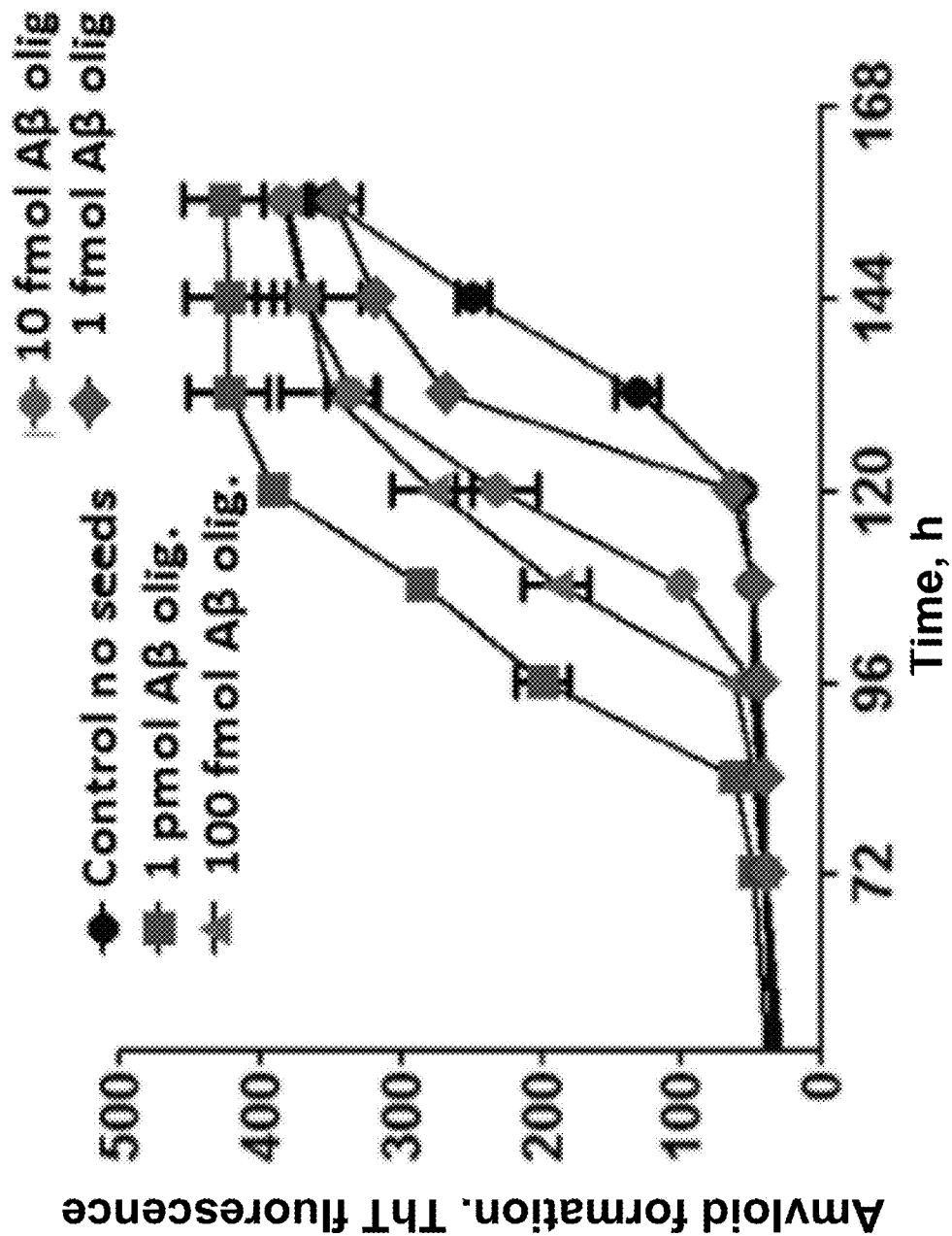
FIG. 10 is a graph of amyloid formation versus time showing the acceleration of Aβ aggregation by the presence of different quantities of synthetic oligomers spiked in human plasma.

FIG. 10 is a graph of amyloid formation versus time as measured by Thioflavin T fluorescence showing detection of soluble, misfolded Aβ protein spiked in human plasma. ELISA plates pre-coated with protein G were coated with an anti-conformational antibody (16ADV from Acumen). Thereafter, plates were incubated with human blood plasma (100 μl) as such (control) or spiked with different concentrations of synthetic soluble, misfolded Aβ protein. After incubation, plates were subjected to Aβ-PMCA (29 min incubation and 30 s shaking) in the presence of Aβ40 monomer (2 μM) and ThT (5 μM). Amyloid formation was measured by Thioflavin fluorescence. FIG. 10 is representative of several experiments done with 3 different antibodies which worked similarly.

Figure 11:
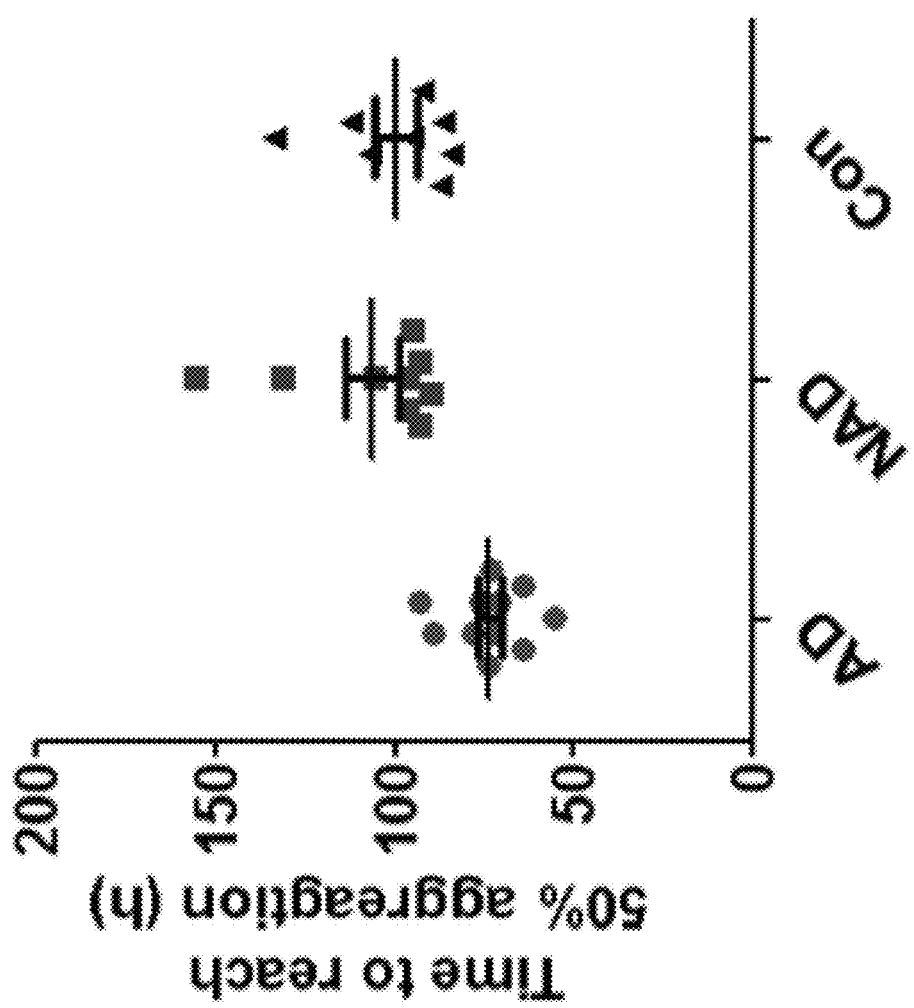
FIG. 11 is a graph showing time to reach 50% aggregation in an Aβ-PMCA assay in the presence of plasma samples from AD patients and controls.

Example 9: Capturing of Soluble Misfolded Aβ from AD Patient Samples Vs Controls FIG. 11 is a graph showing time to reach 50% aggregation in an Aβ-PMCA assay in plasma samples from AD patients and controls. Blood plasma samples from patients affected by AD, non-AD neurodegenerative diseases (NAD), and healthy controls were incubated with anti-Aβ antibody (82E1) coated beads. Aβ-PMCA was carried out as described in EXAMPLE 2. The time needed to reach 50% aggregation was recorded in individual patients in each group. Differences were analyzed by one-way ANOVA followed by the Tukey's post-hoc test. ROC analysis of this data showed a 82% sensitivity and 100% specificity for correctly identifying AD patients from controls.

Example 10: Sonication and Shaking are Effective with Various Detection Methods

Figure 12:
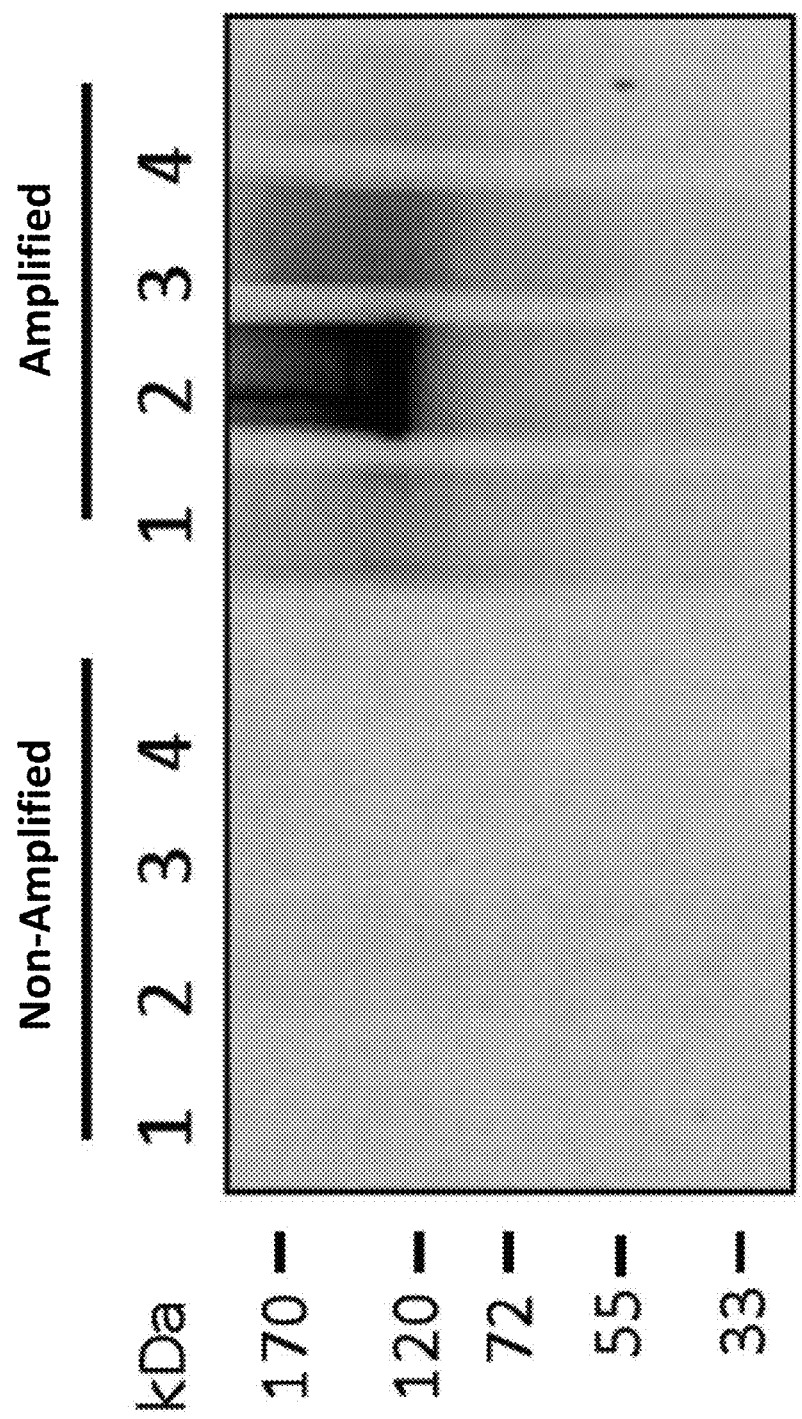
FIG. 12 is a western blot showing the results of amplification of Aβ aggregation by cycles of incubation/sonication in the presence of distinct quantities of synthetic Aβ oligomers monitored by Western blot after protease digestion.

FIG. 12 is a western blot showing the results of amplification of Aβ aggregation by using sonication instead of shaking as a mean to fragment aggregates. The experiment was done in the presence of distinct quantities of synthetic Aβ oligomers. Samples of 10 μg/ml of seed-free monomeric Aβ1-42 (SEQ ID NO: 3) were incubated alone (lane 1) or with 300 (lane 2), 30 (lane 3) and 3 (lane 4) fmols of, misfolded Aβ. Samples were either frozen without amplification (non-amplified) or subjected to 96 PMCA cycles (amplified), each including 30 min incubation followed by 20 sec sonication. Aggregated Aβ was detected by western blot using anti-Aβ antibody after treatment of the samples with proteinase K (PK). In our experiments, it was observed that detection using thioflavin T fluorescence was not compatible with sonication, but works very well with shaking as a physical disruption method. FIG. 12 shows that using a different detection method for the Aβ aggregates, in this case Western Blotting, sonication works as well as shaking.

Example 11: Production of Monomeric Aβ as PMCA Substrate

Seed-free monomeric Aβ was obtained by size exclusion chromatography. Briefly, an aliquot of a 1 mg/mL peptide solution prepared in dimethylsulfoxide was fractionated using a Superdex 75 column eluted at 0.5 mL/min with 10 mM sodium phosphate at pH 7.5. Peaks will be detected by UV absorbance at 220 nm. The peak corresponding to 4-10 kDa molecular weight containing monomer/dimmers of Aβ was collected and concentration determined by amino acid analysis. Samples were stored lyophilized at −80° C.

Example 12: Production and Purification of Aβ

E. coli cells harboring pET28 GroES-Ub-Aβ42 plasmid were grown in Luria broth (LB) at 37° C., and expression was induced with 0.4 mM IPTG. After 4 h, cells were harvested and lysed in a lysis buffer (20 mM Tris-Cl, pH 8.0, 10 mM NaCl, 0.1 mM PMSF, 0.1 mM EDTA and 1 mM β-mercaptoethanol) and centrifuged at 18,000 rpm for 30 min. Inclusion bodies were re-suspended in a resuspension buffer (50 mM Tris-Cl, pH 8.0, 150 mM NaCl, and 1 mM DTT) containing 6 M urea. Insoluble protein was removed by centrifugation at 18,000 rpm for 30 min. The supernatant containing GroES-Ub-Aβ42 fusion protein will be collected. To cleave off Aβ42 from fusion protein, the fusion protein was diluted 2-fold with resuspension buffer and treated with recombinant de-ubiquinating enzyme (Usp2cc) 1:100 enzyme to substrate molar ratio at 37° C. for 2 h. After that, samples was loaded on a C18 column (25 mm×250 mm, Grace Vydac, USA). Aβ42 was purified with a solvent system buffer 1 (30 mM ammonium acetate, pH 10, 2% acetonitrile) and buffer 2 (70% acetonitrile) at a flow rate 10 ml/min using a 20-40% linear gradient of buffer 2 over 35 min. Purified Aβ42 was lyophilized and stored at −80° C., until use.

To the extent that the term "includes" or "including" is used in the specification or the claims, it is intended to be inclusive in a manner similar to the term "comprising" as that term is interpreted when employed as a transitional word in a claim. Furthermore, to the extent that the term "or" is employed (e.g., A or B) it is intended to mean "A or B or both." When the applicants intend to indicate "only A or B but not both" then the term "only A or B but not both" will be employed. Thus, use of the term "or" herein is the inclusive, and not the exclusive use. See Bryan A. Garner, A Dictionary of Modern Legal Usage 624 (2d. Ed. 1995). Also, to the extent that the terms "in" or "into" are used in the specification or the claims, it is intended to additionally mean "on" or "onto." To the extent that the term "selectively" is used in the specification or the claims, it is intended to refer to a condition of a component wherein a user of the apparatus may activate or deactivate the feature or function of the component as is necessary or desired in use of the apparatus. To the extent that the term "operatively connected" is used in the specification or the claims, it is intended to mean that the identified components are connected in a way to perform a designated function. To the extent that the term "substantially" is used in the specification or the claims, it is intended to mean that the identified components have the relation or qualities indicated with degree of error as would be acceptable in the subject industry.

As used in the specification and the claims, the singular forms "a," "an," and "the" include the plural unless the singular is expressly specified. For example, reference to "a compound" may include a mixture of two or more compounds, as well as a single compound.

As used herein, the term "about" in conjunction with a number is intended to include ±10% of the number. In other words, "about 10" may mean from 9 to 11.

As used herein, the terms "optional" and "optionally" mean that the subsequently described circumstance may or may not occur, so that the description includes instances where the circumstance occurs and instances where it does not.

In addition, where features or aspects of the disclosure are described in terms of Markush groups, those skilled in the art will recognize that the disclosure is also thereby described in terms of any individual member or subgroup of members of the Markush group. As will be understood by one skilled in the art, for any and all purposes, such as in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, and the like. As a non-limiting example, each range discussed herein can be readily broken down into a lower third, middle third and upper third, and the like. As will also be understood by one skilled in the art all language such as "up to," "at least," "greater than," "less than," include the number recited and refer to ranges which can be subsequently broken down into sub-ranges as discussed above. Finally, as will be understood by one skilled in the art, a range includes each individual member. For example, a group having 1-3 cells refers to groups having 1, 2, or 3 cells. Similarly, a group having 1-5 cells refers to groups having 1, 2, 3, 4, or 5 cells, and so forth. While various aspects and embodiments have been disclosed herein, other aspects and embodiments will be apparent to those skilled in the art.

As stated above, while the present application has been illustrated by the description of embodiments thereof, and while the embodiments have been described in considerable detail, it is not the intention of the applicants to restrict or in any way limit the scope of the appended claims to such detail. Additional advantages and modifications will readily appear to those skilled in the art, having the benefit of the present application. Therefore, the application, in its broader aspects, is not limited to the specific details, illustrative examples shown, or any apparatus referred to. Departures may be made from such details, examples, and apparatuses without departing from the spirit or scope of the general inventive concept.

The various aspects and embodiments disclosed herein are for purposes of illustration and are not intended to be limiting, with the true scope and spirit being indicated by the following claims.

The invention claimed is:

1. A method for determining a presence of a soluble, misfolded Aβ protein in a sample, comprising:
   contacting the sample with a monomeric, folded Aβ protein in the presence of a biological fluid to form an incubation mixture, the incubation mixture comprising the monomeric, folded Aβ protein in a concentration range of about 1 μM to about 10 μM;
   providing a buffer in the incubation mixture, the buffer comprising one of: Tris-HCL, MES, PIPES, MOPS, BES, TES, and HEPES;
   conducting an incubation cycle two or more times on the incubation mixture effective to form an amplified portion of misfolded Aβ protein from the monomeric, folded Aβ protein, each incubation cycle comprising:
   incubating the incubation mixture effective to cause misfolding and/or aggregation of at least a portion of the monomeric, folded Aβ protein in the presence of the soluble, misfolded Aβ protein, the incubating being conducted at a temperature between about 12° C. and about 30° C.;
   physically disrupting the incubation mixture effective to at least partly de-aggregate at least a portion of a misfolded Aβ aggregate present; and
   determining the presence of the soluble, misfolded Aβ protein in the sample by detecting at least a portion of the amplified portion of misfolded Aβ protein,
   the soluble, misfolded Aβ protein comprising one or more of: a soluble, misfolded Aβ monomer and a soluble, misfolded Aβ aggregate; and
   the amplified portion of misfolded Aβ protein comprising one or more of: an amplified portion of the soluble, misfolded Aβ monomer, an amplified portion of the soluble, misfolded Aβ aggregate, and an insoluble, misfolded Aβ aggregate.

2. The method of claim 1:
   further comprising contacting an indicator of misfolded Aβ protein to the incubation mixture, the indicator of misfolded Aβ protein being characterized by an indicating state in the presence of misfolded Aβ protein and a non-indicating state in the absence of misfolded Aβ protein; and
   wherein the determining the presence of the soluble, misfolded Aβ protein in the sample comprises detecting the indicating state of the indicator of misfolded Aβ protein in the incubation mixture.

3. The method of claim 2, the indicator of misfolded Aβ protein comprising one or more of: Thioflavin T, Congo Red, m-I-Stilbene, Chrysamine G, PIB, BF-227, X-34, TZDM, FDDNP, MeO-X-04, IMPY, NIAD-4, luminescent conjugated polythiophenes, a fluorescent protein, and derivatives thereof.

4. The method of claim 1, the determining the presence of the soluble, misfolded Aβ protein in the sample comprising one or more of:
   determining an amount of the soluble, misfolded Aβ protein in the sample;
   determining the amount of the soluble, misfolded Aβ protein in the sample at a sensitivity of at least about 80%;
   determining the amount of the soluble, misfolded Aβ protein in the sample at less than about 100 nmol;
   determining the amount of the soluble, misfolded Aβ protein in the sample in a molar ratio to monomeric, folded Aβ protein comprised by the sample, the molar ratio being less than about 1:100;
   determining the soluble, misfolded Aβ protein in the sample with a specificity of at least about 80%; and determining an amount of the soluble, misfolded Aβ protein in the sample compared to a control sample.

5. The method of claim 1, the incubating comprising incubating the incubation mixture at between about 18° C. and about 26° C.

6. The method of claim 1, the detecting at least the portion of the amplified portion of misfolded Aβ protein comprising one or more of: a Western Blot assay, a dot blot assay, an enzyme-linked immunosorbent assay (ELISA), a thioflavin T binding assay, a Congo Red binding assay, a sedimentation assay, electron microscopy, atomic force microscopy, surface plasmon resonance, and spectroscopy.

7. The method of claim 1, further comprising providing the monomeric, folded Aβ protein in labeled form, the detecting at least the portion of the amplified portion of misfolded Aβ protein comprising detecting the monomeric, folded Aβ protein in labeled form as incorporated into the amplified portion of misfolded Aβ protein.

8. The method of claim 1, the sample being taken from a subject, further comprising determining or diagnosing one or more of:
the presence of AD (Alzheimer's disease) in the subject according to the presence of the soluble, misfolded Aβ protein in the sample;
the presence of AD in the subject according to the presence of the soluble, misfolded Aβ protein in the sample compared to a control sample taken from a control subject;
the presence of AD in the subject by comparing an amount of the soluble, misfolded Aβ protein in the sample to a predetermined threshold amount, the detecting at least the portion of the amplified portion of misfolded Aβ protein comprising detecting an amount of the soluble, misfolded Aβ protein in the sample;
the presence of AD in the subject according to the presence of the soluble, misfolded Aβ protein in the sample, the subject exhibiting no clinical signs of dementia according to cognitive testing;
the presence of AD in the subject according to the presence of the soluble, misfolded Aβ protein in the sample, the subject exhibiting no cortex plaques or tangles according to amyloid beta contrast imaging;
the presence of AD as a contributing factor to one or more clinical signs of dementia in the subject according to the presence of the soluble, misfolded Aβ protein in the sample, the subject exhibiting the one or more clinical signs of dementia according to cognitive testing; and
a progression or homeostasis of AD in the subject by comparing the amount of the soluble, misfolded Aβ protein in the sample to an amount of the soluble, misfolded Aβ protein in a comparison sample taken from the subject at a different time compared to the sample.

9. The method of claim 1, further comprising obtaining the sample from a subject,
the sample comprising one or more of: amniotic fluid; bile; blood; cerebrospinal fluid; cerumen; skin; exudate; feces; gastric fluid; lymph; milk; mucus; mucosal membrane; nasal secretions; peritoneal fluid; plasma; pleural fluid; pus; saliva; sebum; semen; sweat; synovial fluid; tears; and urine; and
the subject being one of a: human, mouse, rat, dog, cat, cattle, horse, deer, elk, sheep, goat, pig, and non-human primate.

10. The method of claim 1, further comprising:
comparing the amount of the soluble, misfolded Aβ protein in the sample to an amount of the soluble, misfolded Aβ protein in a comparison sample, the sample and the comparison sample being taken from a subject being treated with an Aβ modulating therapy, the sample and the comparison sample being taken from the subject at different times over a period of time under the Aβ modulating therapy; and
determining the subject is one of: responsive to the Aβ modulating therapy according to a change in the soluble, misfolded Aβ protein over the period of time, or non-responsive to the Aβ modulating therapy according to homeostasis of the soluble, misfolded Aβ protein over the period of time.

11. The method of claim 1, the sample being taken from a subject, the subject being treated with an Aβ modulating therapy, the Aβ modulating therapy comprising administration of one or more of: an inhibitor of BACE1 (beta-secretase 1); an inhibitor of γ-secretase; a modulator of Aβ homeostasis; E2609; MK-8931; LY2886721; AZD3293; semagacestat (LY-450139); avagacestat (BMS-708163); solanezumab; (SEQ ID NO: 11 (VH))(SEQ ID NO: 12 (VL)); crenezumab (SEQ ID NO: 13 (VH))(SEQ ID NO: 14 (VL)); bapineuzumab (SEQ ID NO: 15 (VH))(SEQ ID NO: 16 (VL)); BIIB037 (SEQ ID NO: 17 (VH))(SEQ ID NO: 18 (VL)); CAD106; antibodies raised against Aβ globulomers; ACC-001; V950; and Affitrope AD02.

12. The method of claim 1, the physically disrupting the incubation mixture comprising one or more of: sonication, stirring, shaking, freezing/thawing, laser irradiation, autoclave incubation, high pressure, homogenization, and cyclic agitation.

13. The method of claim 1, the monomeric, folded Aβ protein and/or the soluble, misfolded Aβ protein comprising peptides formed via β- or γ-secretase cleavage of one or more of: amyloid precursor protein (SEQ ID NO: 1); Abeta40 (SEQ ID NO: 2); and Abeta42 (SEQ ID NO: 3).

14. The method of claim 1, comprising:
contacting the sample with Thioflavin T and the monomeric, folded Aβ protein to form the incubation mixture;
conducting the incubation cycle two or more times on the incubation mixture effective to form the amplified portion of misfolded Aβ protein from the monomeric, folded Aβ protein, each incubation cycle comprising:
incubating the incubation mixture effective to cause misfolding and/or aggregation of at least the portion of the monomeric, folded Aβ protein in the presence of the soluble, misfolded Aβ protein;
shaking the incubation mixture effective to at least partly de-aggregate at least the portion of a misfolded Aβ aggregate present; and
determining the presence of the soluble, misfolded Aβ protein in the sample by detecting a fluorescence of the Thioflavin T corresponding to at least the portion of the amplified portion of misfolded Aβ protein.

15. A method for determining a presence of a soluble, misfolded Aβ protein in a sample, comprising:
capturing a soluble, misfolded Aβ protein from the sample to form a captured soluble, misfolded Aβ protein;
contacting the captured, soluble misfolded Aβ protein with a molar excess of monomeric, folded Aβ protein to form an incubation mixture, the molar excess being greater than an amount of Aβ protein monomer included in the captured soluble, misfolded Aβ protein, the incubation mixture comprising the monomeric, folded AB protein in a concentration range of about 1 µM to about 10 µM;

providing a buffer in the incubation mixture, the buffer comprising one of: Tris-HCL, MES, PIPES, MOPS, BES, TES, and HEPES;

conducting an incubation cycle two or more times on the incubation mixture effective to form an amplified portion of misfolded Aβ protein from the monomeric, folded Aβ protein, each incubation cycle comprising:

incubating the incubation mixture effective to cause misfolding and/or aggregation of at least a portion of the monomeric, folded Aβ protein in the presence of the captured soluble, misfolded Aβ protein, the incubating being conducted at a temperature between about 12° C. and about 30° C.;

physically disrupting the incubation mixture effective to at least partly de-aggregate at least a portion of a misfolded Aβ aggregate present; and determining the presence of the soluble, misfolded Aβ protein in the sample by detecting at least a portion of the amplified portion of misfolded Aβ protein, the soluble, misfolded Aβ protein comprising one or more of: a soluble, misfolded Aβ monomer and a soluble, misfolded Aβ aggregate; and the captured, soluble, misfolded Aβ protein comprising one or more of: a captured, soluble, misfolded Aβ monomer and a captured, soluble, misfolded Aβ aggregate; and the amplified portion of misfolded Aβ protein comprising one or more of: an amplified portion of the soluble, misfolded Aβ monomer, an amplified portion of the soluble, misfolded Aβ aggregate, and an insoluble, misfolded Aβ aggregate.

16. The method of claim 15, the capturing comprising selectively concentrating the soluble, misfolded Aβ protein in one or more of the sample and the incubation mixture.

17. The method of claim 16, the selectively concentrating the soluble, misfolded Aβ protein comprising one or more of: pre-treating the sample prior to forming the incubation mixture and pre-treating the incubation mixture prior to incubating the incubation mixture.

18. The method of claim 16, the selectively concentrating the soluble, misfolded Aβ protein comprising contacting one or more Aβ specific antibodies to the soluble, misfolded Aβ protein to form a captured soluble, misfolded Aβ protein, the one or more Aβ specific antibodies comprising one or more of: 6E10, 4G8, 82E1, A11, X-40/42, 16ADV, an antibody specific for an amino acid sequence of Aβ, and an antibody specific for a conformation of the soluble, misfolded Aβ protein.

19. The method of claim 18, the one or more Aβ specific antibodies being coupled to a solid phase.

20. The method of claim 19, the solid phase comprising one or more of a magnetic bead and a multiwell plate.

21. The method of claim 15, further comprising:

comparing the amount of the soluble, misfolded Aβ protein in the sample to an amount of the soluble, misfolded Aβ protein in a comparison sample, the sample and the comparison sample being taken from a subject being treated with an Aβ modulating therapy, the sample and the comparison sample being taken from the subject at different times over a period of time under the Aβ modulating therapy; and determining the subject is one of: responsive to the Aβ modulating therapy according to a change in the soluble, misfolded Aβ protein over the period of time, or non-responsive to the Aβ modulating therapy according to homeostasis of the soluble, misfolded Aβ protein over the period of time.

22. The method of claim 15, the sample being taken from a subject, further comprising determining or diagnosing one or more of:

the presence of AD in the subject according to the presence of the soluble, misfolded Aβ protein in the sample;

the presence of AD in the subject according to the presence of the soluble, misfolded Aβ protein in the sample compared to a control sample taken from a control subject;

the presence of AD in the subject by comparing an amount of the soluble, misfolded Aβ protein in the sample to a predetermined threshold amount, the detecting at least the portion of the amplified portion of misfolded Aβ protein comprising detecting an amount of the soluble, misfolded Aβ protein in the sample;

the presence of AD in the subject according to the presence of the soluble, misfolded Aβ protein in the sample, the subject exhibiting no clinical signs of dementia according to cognitive testing;

the presence of AD in the subject according to the presence of the soluble, misfolded Aβ protein in the sample, the subject exhibiting no cortex plaques or tangles according to amyloid beta contrast imaging;

the presence of AD as a contributing factor to one or more clinical signs of dementia in the subject according to the presence of the soluble, misfolded Aβ protein in the sample, the subject exhibiting the one or more clinical signs of dementia according to cognitive testing; and a progression or homeostasis of AD in the subject by comparing the amount of the soluble, misfolded Aβ protein in the sample to an amount of the soluble, misfolded Aβ protein in a comparison sample taken from the subject at a different time compared to the sample.

* * * * *